US011656227B2

(12) United States Patent
Sasso et al.

(10) Patent No.: US 11,656,227 B2
(45) Date of Patent: May 23, 2023

(54) BIOMARKERS AND METHODS FOR ASSESSING PSORIATIC ARTHRITIS DISEASE ACTIVITY

(71) Applicants: Crescendo Bioscience, South San Francisco, CA (US); The Regents of the University of California, La Jolla, CA (US)

(72) Inventors: Eric Sasso, South San Francisco, CA (US); Paul Scott Eastman, South San Francisco, CA (US); Rebecca Bolce, South San Francisco, CA (US); Arthur Kavanaugh, San Diego, CA (US)

( * ) Notice: Subject to any disclaimer, the term of this patent is extended or adjusted under 35 U.S.C. 154(b) by 0 days.

(21) Appl. No.: 15/938,728

(22) Filed: Mar. 28, 2018

(65) Prior Publication Data

US 2018/0217143 A1    Aug. 2, 2018

Related U.S. Application Data

(63) Continuation of application No. PCT/US2016/054323, filed on Sep. 29, 2016.

(60) Provisional application No. 62/234,526, filed on Sep. 29, 2015.

(51) Int. Cl.
| | | |
|---|---|---|
| *G01N 33/564* | (2006.01) | |
| *G01N 33/68* | (2006.01) | |
| *G01N 33/53* | (2006.01) | |
| *G01N 33/566* | (2006.01) | |
| *G16B 25/00* | (2019.01) | |
| *G16B 20/00* | (2019.01) | |
| *G16B 25/10* | (2019.01) | |
| *G16B 20/20* | (2019.01) | |
| *G16H 50/50* | (2018.01) | |
| *G16H 50/20* | (2018.01) | |
| *G01N 33/531* | (2006.01) | |

(52) U.S. Cl.
CPC ........... *G01N 33/566* (2013.01); *G01N 33/53* (2013.01); *G01N 33/531* (2013.01); *G01N 33/564* (2013.01); *G01N 33/68* (2013.01); *G01N 33/6893* (2013.01); *G16B 20/00* (2019.02); *G16B 20/20* (2019.02); *G16B 25/00* (2019.02); *G16B 25/10* (2019.02); *G16H 50/20* (2018.01); *G16H 50/50* (2018.01); *G01N 2800/102* (2013.01); *G01N 2800/60* (2013.01)

(58) Field of Classification Search
CPC ................................ G01N 33/53; A61K 38/00
See application file for complete search history.

(56) References Cited

U.S. PATENT DOCUMENTS

| | | | |
|---|---|---|---|
| 4,230,797 A | 10/1980 | Boguslaski et al. | |
| 4,233,402 A | 11/1980 | Maggio et al. | |
| 4,275,149 A | 6/1981 | Litman et al. | |
| 4,376,110 A | 3/1983 | David et al. | |
| 4,659,678 A | 4/1987 | Forrest et al. | |
| 4,727,022 A | 2/1988 | Skold et al. | |
| 5,018,067 A | 5/1991 | Mohlenbrock et al. | |
| 5,744,305 A | 4/1998 | Fodor et al. | |
| 3,058,013 A1 | 11/2011 | Karl et al. | |
| 2002/0038227 A1 | 3/2002 | Fey et al. | |
| 2004/0122296 A1 | 6/2004 | Hatlestad et al. | |
| 2004/0122297 A1 | 6/2004 | Stahmann et al. | |
| 2005/0142569 A1 | 6/2005 | Guild et al. | |
| 2006/0094056 A1 | 5/2006 | Chappell et al. | |
| 2006/0286586 A1 | 12/2006 | Drexhage et al. | |
| 2007/0172888 A1 | 7/2007 | Hallermayer et al. | |
| 2008/0026485 A1 | 1/2008 | Hueber et al. | |
| 2009/0017472 A1 | 1/2009 | Stuhlmuller et al. | |
| 2009/0114627 A1 | 5/2009 | Nakamura | |
| 2009/0142792 A1 | 6/2009 | Robinson et al. | |
| 2009/0270272 A1 | 10/2009 | Karl et al. | |
| 2011/0137851 A1* | 6/2011 | Cavet ................... | C12Q 1/6883 706/54 |
| 2011/0251099 A1 | 10/2011 | Visvanathan et al. | |
| 2011/0269633 A1 | 11/2011 | Bilello et al. | |
| 2012/0178100 A1* | 7/2012 | Wagner .................... | C12Q 1/42 435/7.4 |
| 2012/0258883 A1 | 10/2012 | Chappell et al. | |
| 2013/0052665 A1 | 2/2013 | Ling et al. | |
| 2014/0005071 A1 | 1/2014 | Chappell et al. | |
| 2014/0142861 A1 | 5/2014 | Hagstrom et al. | |

FOREIGN PATENT DOCUMENTS

| | | |
|---|---|---|
| JP | 2007506100 | 3/2007 |
| JP | 2008545960 | 12/2008 |
| JP | 2009524807 | 7/2009 |
| JP | 2010506147 | 2/2010 |
| JP | 2011520095 | 7/2011 |
| JP | 2013508687 | 3/2013 |
| WO | 2004056456 | 7/2004 |
| WO | 2004088309 | 10/2004 |
| WO | 2005029091 | 3/2005 |
| WO | 2006125973 | 11/2006 |
| WO | 2007039280 | 4/2007 |
| WO | 2007085411 | 8/2007 |
| WO | 2007089303 | 8/2007 |
| WO | 2007/123976 | 11/2007 |
| WO | 2007123976 | 11/2007 |
| WO | 2008037420 | 4/2008 |
| WO | 2009114627 | 9/2009 |
| WO | 2012/061821 | 5/2012 |

(Continued)

OTHER PUBLICATIONS

Connolly et al., Arthritis Rheum., 2012, vol. 64(4): 1035-1045.*

(Continued)

*Primary Examiner* — Xiaozhen Xie
(74) *Attorney, Agent, or Firm* — Kilpatrick Townsend & Stockton LLP

(57) ABSTRACT

Provided herein are biomarkers and methods for generating scores useful for assessing psoriatic arthritis (PsA) disease activity in subjects previously diagnosed with PsA. The invention also provides predictive model methods based on the biomarkers, as well as computer systems, software embodiments of the models for scoring and optionally classifying samples, and methods of recommending optimal therapeutic regimens.

13 Claims, 3 Drawing Sheets

(56) References Cited

FOREIGN PATENT DOCUMENTS

| WO | 2012061821 | 5/2012 |
|---|---|---|
| WO | 2013167727 | 11/2013 |
| WO | 2014118550 | 8/2014 |
| WO | 2015132241 | 9/2015 |
| WO | 2015191423 | 12/2015 |

OTHER PUBLICATIONS

Nash et al., Ann. Rheum. Dis., 2005, vol. 64(Suppl. II):ii74-ii77.*
Jensen et al., J. Eur. Acad. Dermatol. Venereol., 2013, vol. 27(7):815-819 (abstract).*
G.H. Sack, Jr., Molecular Medicine, 2018, vol. 24, Article No. 46.*
Afuwape et al., Histol. Histopathol., 2002, vol. 17, pp. 961-972.
Aletaha et al., Arth. Rheum. 2005, vol. 52, No. 9, pp. 2625-2636.
Australian Office Action from Application No. 20110306593, dated May 1, 2015.
Australian Office Action from Application No. 20110306593, dated Dec. 2, 2014.
Australian Office Action Response from Application No. 2010306593, dated Feb. 19, 2015.
Baecklund et al., Arth. Rheum., 2006, vol. 54, No. 3, pp. 692-701.
Banerjee et al., Am. J. Cardiol., 2008, vol. 101, No. 8, pp. 1201-1205.
Benjamini et al., J. Royal Stat. Soc. B, 1995, vol. 57, No. 1, pp. 289-300.
Berk, Springer, 2008, p. 213.
Breedveld et al., Arth. Rheum., 2006, vol. 54, No. 1, pp. 26-37.
Breiman, Machine Learning, 2001, vol. 45, No. 1, pp. 5-32.
Brown et al., Arth. Rheum., 2006, vol. 54, pp. 3761-3773.
Brown et al., Arth. Rheum., 2008, vol. 58, No. 10, pp. 2958-2967.
Busquets-Perez et al., Expert Opinion on Emerging Drugs, 2013, vol. 18, No. 1, pp. 71-86.
Canadian Office Action from Application No. 2,777,800, dated Nov. 7, 2016.
Canadian Office Action from Application No. 2,777,800, dated Sep. 14, 2017.
Canadian Office Action from Application No. 2,777,800, dated Dec. 21, 2015.
Canadian Office Action Response from Application No. 2,777,800, dated Mar. 14, 2018.
Canadian Office Action Response from Application No. 2,777,800, dated Jun. 16, 2016.
Canadian Office Action Response from Application No. 2,777,800, dated Apr. 28, 2017.
Centola et al., PLoS One, 2013, vol. 8, No. 4, pp. e606635.
Chan et al., ed. M. Matucci Cerinic. Exp. Rheum., 2002, vol. 20, No. 4, pp. 443-444.
Chandran et al., The Journal of Rheumatology, 2012, vol. 89, pp. 65-66.
Chinese First Office Action, Chinese Application No. 201080057651.4, dated Jun. 21, 2013.
Chinese Second Office Action, Chinese Application No. 201080057651.4, dated Jan. 13, 2014.
Churchman et al., Ann. Rheum. Dis., 2009, vol. 68, pp. A1-A56, Abstract A77.
Coffman et al., Critical Reviews in Clinical Laboratory Sciences, 2008, vol. 46, No. 6, pp. 531-562.
Cohen et al., Ann. Rheum. Dis., 2007, vol. 66, pp. 358-363.
Consolaro et al., Arthritis & Rheumatism, 2009, vol. 61, No. 5, pp. 658-666.
Duurland et al., Current Rheumatology Reports, 2014, vol. 16, No. 3, pp. 1-6, Article No. 406.
European Communication from Application No. 10824227.2, dated Mar. 9, 2018.
European Communication from Application No. 10824227.2, dated May 29, 2017.
European Communication Response from Application No. 10824227.2, dated May 10, 2018.
European Communication Response from Application No. 10824227.2, dated Sep. 25, 2017.
European Communication Response from Application No. 10824227.2, dated Oct. 26, 2015.
European Communication Response from Application No. 15772723.1, dated Apr. 12, 2017.
European Communication Response from Application No. 15806913.8, dated Jun. 6, 2017.
Extended European Search Report for Application No. 10824227.2, dated May 8, 2015.
Extended European Search Report for Application No. 15772723.1, dated Jul. 28, 2017.
Felson d.T. et al., Arthritis & Rheumatism, 1993, vol. 36, No. 6, pp. 729-740.
Felson d.T. et al., Arthritis & Rheumatism, 1995, vol. 38, No. 6, pp. 727-735.
Fransen J. et al., Arthritis Care and Research, 2010, vol. 62, No. 10, pp. 1392-1398.
Goekoop-Ruiterman et al., Ann. Rheum. Dis., 2010, vol. 69, pp. 65-69.
Goekoop-Ruiterman et al., Arth. Rheum. 2005, vol. 52, pp. 3381-3390.
Goodson et al., Ann. Rheum. Dis., 2005, vol. 64, No. 11, pp. 1595-1601.
Gossec L. et al., Ann. Rheum. Dis., 2004, vol. 63, No. 6, pp. 675-680.
Green et al., Rheumatology, 2003, vol. 42, pp. 83-88.
Grigor C. et al., Lancet, 2004, vol. 364, pp. 263-269.
Guler-Yuksel M. et al., Ann. Rheum. Dis., 2009, vol. 68, pp. 330-336.
Hueber et al., Arthritis & Rheumatism, 2005, vol. 52, pp. 2645-2655.
Beukelman et al. 2011. 63:465-482 (Year: 2011).
European Communication Response from Application No. 16852551.7, dated Oct. 31, 2018, 2 pages.
Jeffrey R. 2010. Medicine 38:167-171 (Year: 2010).
Petty et al. 2004. J. Rhematol. 31 :390-392 (Year: 2004).
Pisetsky et al. 2012. Best Pract Res. Clin. Rheumatol. 26:251-261 (Year: 2012).
International Preliminary Report on Patentability from Application No. PCT/US2010/052970, dated Dec. 16, 2010.
International Preliminary Report on Patentability from Application No. PCT/US2015/023302, dated Oct. 13, 2016.
International Preliminary Report on Patentability from Application No. PCT/US2015/034631, dated Dec. 22, 2016.
International Preliminary Report on Patentability from Application No. PCT/US2015/034945, dated Dec. 22, 2016.
International Preliminary Report on Patentability from Application No. PCT/US2016/054323, dated Apr. 12, 2018.
International Search Report from Application No. PCT/US2010/052970, dated Dec. 16, 2010.
International Search Report from Application No. PCT/US2015/023302, dated Jun. 25, 2015.
International Search Report from Application No. PCT/US2015/034631, dated Aug. 28, 2015.
International Search Report from Application No. PCT/US2015/034945, dated Aug. 24, 2015.
International Search Report from Application No. PCT/US2016/054318, dated Jan. 13, 2017.
International Search Report from Application No. PCT/US2016/054323, dated Dec. 8, 2016.
International Search Report from Application No. PCT/US2017/020181, dated Jun. 12, 2017.
Japanese Office Action from Japanese Application No. 2012-534431, dated May 28, 2014.
Japanese Office Action from Japanese Application No. 2012-534431, dated Sep. 8, 14.
Japanese Office Action Response from Japanese Application No. 2012-534431, dated Aug. 14, 2014.
Japanese Office Action Response from Japanese Application No. 2012-534431, dated Oct. 17, 2014.
Jarvis J. et al., Lancet, 2005, vol. 365, pp. 199-200.
Johansen et al., Rheumatology, 1999, vol. 38, pp. 618-626.

(56) References Cited

OTHER PUBLICATIONS

Khan N.A, et al., ACR/ARHP Scientific Meeting, 2008, abstract.
Kievit et al., Ann. Rheum. Dis., 2008, vol. 67, No. 9, pp. 1229-1234.
Klooster et al., Arthritis Research Ther., 2005, vol. 7, pp. R127-R138.
Kroot E.J.A. et al., Arthritis & Rheumatism, 2000, vol. 43, No. 8, pp. 1831-1835.
Lipsky et al., iV. Engl. J. Med., 2000, vol. 343, pp. 1594-1602.
Makinen et al., Ann. Rheum. Dis., 2005, vol. 64, No. 10, pp. 1410-1413.
Maksymowych et al., American College of Rheumatology/The Association of Rheumatology Health Professionals (ACR/ARHP) Annual Meeting, Boston, MA, 2014, poster No. 2615.
Mallya R.K. et al., The Journal of Rheumatology, 1982, vol. 9, No. 2, pp. 224-228.
Miller et al., Pediatric Rheumatology, 2011, vol. 9, No. 9, pp. 1-7.
Morel et al., The Journal of Biol. Chem., 2002, vol. 277, pp. 34679-34691.
Mottonen et al., Arth. Rheum., 2002, vol. 46, No. 4, pp. 894-898.
Nadareishvili Z. et al., Arthritis Rheum., 2008, vol. 59, No. 8, pp. 1090-1096.
Partial European Search Report for Application No. 10824227.2, dated Jan. 12, 2015.
Partial European Search Report for Application No. 15806913.8, dated Nov. 10, 2017.
Pearson T.A. et al., Circulation, 2003, pp. 499-511.
Pedersen et al., Annals of the Rheumatic Diseases, 2011, vol. 70, No. 8, pp. 1375-1381.
Pettit et al., Am. J. Pathol., 2001, vol. 159, pp. 1689-1699.
Pincus T. et al., Clin. Exp. Rheum., 2004, vol. 22, Suppl. 35, pp. S50-S56.
Plant M.J. et al., Arthritis & Rheumatism, 2000, vol. 43, No. 7, pp. 1473-1477.
Prakken et al., The Lancet, 2011, vol. 377, No. 9783, pp. 2138-2149.
Prevoo M.L.L et al., Arthritis & Rheumatism, 1995, vol. 38, No. 1, pp. 44-48.
Ranganath et al., J. Rheum., 2008, vol. 35, pp. 1966-1971.
Ridker P.M. et al., The New England Journal of Medicine, 2000, vol. 342, No. 12, pp. 836-843.
Ringold et al., Annals of the Rheumatic Diseases, 2014, vol. 73, No. Suppl. 2, p. 587.3-588.
Ringold et al., Arthritis & Rheumatology, 2014, vol. 66, pp. S10-S11.
Ritchlin, The Journal of Rheumatology, 2012, vol. 89, pp. 57-60.
Schierbeck et al., J. Rheumatol., 2013, vol. 40, pp. 1604-1613.
Senolt et al., Ann. Rheum. Dis., 2007, vol. 66, pp. 458-463.
Shimizu et al., Cytokine, 2013, vol. 61, pp. 345-348.
Smolen et al., Arth. Rheum., 2005, vol. 52, No. 4, pp. 1020-1030.
Smolen et al., Arthritis Research Therapy, 2008, vol. 10, pp. 208-219.
Smolen S. et al., Rheumatology, 2003, vol. 42, pp. 244-257.
Sokka et al., Clin. Exp. Rheum., 2006, vol. 24, Suppl. 43, pp. S74-S76.
Stucki G. et al., Arthritis & Rheumatism, 1995, vol. 38, No. 6, pp. 795-798.
Taylor et al., Arth. Rheum., 2004, vol. 50, No. 4, pp. 1107-1116.
Tibshirani, J. Royal Stat. Soc., Series B, 1996, vol. 58, No. 1, pp. 267-288.
Tilleman et al., Proteo, 2005, vol. 5, No. 8, pp. 2247-2257.
Toonen et al., Annals of the Rheumatic Diseases 200812 GB, 2008, vol. 67, No. 12, pp. 1663-1669.
Van den Berg et al., Arth. Rheum., 2005, vol. 52, pp. 995-999.
Van Den Broek et al., Expert Opinion on Biological Therapy 200811 GB, 2008, vol. 8, No. 11, pp. 1773-1785.
Van der Heijde et al., Ann. Rheum. Dis., 1990, vol. 49, No. 11, pp. 916-920.
Van Gestel A.M et al., Arthritis & Rheumatism, 1998, vol. 41, No. 10, pp. 1845-1850.
Van Leeuwen et al., Br. J. Rheum., 1993, vol. 32, suppl., pp. 9-13.
Van Tuyl et al., Ann. Rheum. Dis., 2008, vol. 67, pp. 1574-1577.
Vasan, Circulation, 2006, vol. 113, No. 19, pp. 2335-2362.
Verstappen S.M.M. et al., Ann. Rheum. Dis., 2007, vol. 66, pp. 1443-1449.
Visser, H. et al., Arthritis & Rheumatism, 2002,vol. 46, No. 2, pp. 357-365.
Visvanathan et al., Annals of the Rhuematic Diseases, 2008, vol. 67, No. 4, pp. 511-517.
Weinblatt et al., N. Engl. J. Med., 1999, vol. 340, pp. 253-259.
Wells G. et al., Ann. Rheum. Dis., 2009, vol. 68, pp. 954-960.
Wisiowska et al., Rheumatol. International, 2007, vol. 27, pp. 947-954.
Wolfe F., Arthritis & Rheumatism, 2000, vol. 43, No. 12, pp. 2751-2761.
Wolfe F., The Journal of Rheumatology, 1997, vol. 24, No. 8, pp. 1477-1485.
Zatarain and V. Strand, Nat. Clin. Pract. Rheum., 2006, vol. 2, No. 11, pp. 611-618.
Zou, J. Royal Stat. Soc., series B, 2005, vol. 67, No. 2, pp. 301-320.
Chandran, "Soluble biomarkers may differentiate psoriasis from psoriatic arthritis", The Journal of Rheumatology, vol. 89, No. 1, Jul. 1, 2012 (Jul. 1, 2012), pp. 65-66, XP009509109, DOI: 10.3899/JRHEUM.1202470LITC.
Cunnane et al., "Serum Amyloid a in the Assessment of Early Inflammatory Arthritis", Journal of Rheumato, Journal of Rheumatology Publishing Company, CA, vol. 27, No. 1, Jan. 1, 2000 (Jan. 1, 2000), pp. 58-63, XP009004382, ISSN: 0315-162X.
Ebert et al., "Acute phase serum amyloid A induces proinflammatory cytokines and mineralization via toll-like receptor 4 in mesenchymal stem cells", Stem Cell Research, vol. 15, No. 1, Jul. 1, 2015 (Jul. 1, 2015), pp. 231-239, XP55588360, NL ISSN: 1873-5061, DOI: 10.1016/j.scr.2015.06.008.
Extended European Search Report issued in 16852551.7 dated May 22, 2019 (16 pages).
Imai, "YKL-40 is a serum biomarker reflecting the severity of cutaneous lesions in psoriatic arthritis", J. Dermatology, vol. 40, Feb. 11, 2013 (Feb. 11, 2013), p. 294, XP55588487.
Oliviero et al.,: "A comparative study of serum and synovial fluid lipoprotein levels in patients with various arthritides", Clinica Chimica Acta, vol. 413, No. 1-2, Jan. 1, 2012 (Jan. 1, 2012), pp. 303-307, XP55588355, Amsterdam, NL ISSN: 0009-8981, DOI: 10.1016/j.cca.2011.10.019.
Pedersen et al., "Circulating levels of interleukin-6, vascular endothelial growth factor, YKL-40, matrix metalloproteinase-3, and total aggrecan in spondyloarthritis patients during 3 years of treatment with TNF[alpha] inhibitors", Clinical Rheumatology., vol. 29, No. 11, Jul. 18, 2010 (Jul. 18, 2010), pp. 1301-1309, XP055552024, BE ISSN: 0770-3198, DOI: 10.1007/s10067-010-1528-x.
Przepiera-Bedzak et al., "Serum IL-6 and IL-23 Levels and Their Correlation with Angiogenic Cytokines and Disease Activity in Ankylosing Spondylitis, Psoriatic Arthritis, and SAPHO Syndrome", EPO Form 1703 01.91TRI Mediators of Inflammation., vol. 2015, Jan. 1, 2015 (Jan. 1, 2015), pp. 1-7, XP055552197, GB ISSN: 0962-9351, DOI: 10.1155/2015/785705.
Ritchlin, "Biomarker development in psoriatic arthritis", The Journal of Rheumatology, vol. 89, Jan. 2012, pp. 57-60, XP009509110.
Breiman and Friedman, "Predicting Multivariate Responses in Multiple Linear Regression", Journal of the Royal Statistical Society: Series B (Statistical Methodology), 1997, 59(1):3-54.
Curtis et al., "Validation of a novel multibiomarker test to assess rheumatoid arthritis disease activity", Arthritis Care Res (Hoboken). Dec. 2012;64(12):1794-803. doi: 10.1002/acr.21767.
Hambardzumyan et al., "Pretreatment multi-biomarker disease activity score and radiographic progression in early RA: results from the SWEFOT trial", Ann Rheum Dis. Jun. 2015;74(6):1102-9. doi: 10.1136/annrheumdis-2013-204986. Epub May 8, 2014.
Kisner, HJ, "Product development: the making of the Abbott ARCHITECT", Clin Lab Manage Rev. Nov.-Dec. 1997 11(6):419-21. (Abstract Only).
Ognibene et al., "A new modular chemiluminescence immunoassay analyser evaluated", Clin Chern Lab Med. Mar. 2000;38(3):251-60.

(56) References Cited

OTHER PUBLICATIONS

Park et al., "Three-year experience in using total laboratory automation system", Southeast Asian J Trap Med Public Health. 2002;33 Suppl 2:68-73. (Abstract Only).
Pauli et al., "The Abbott Architect c8000: analytical performance and productivity characteristics of a new analyzer applied to general chemistry testing", Clin Lab. 2005;51(1-2):31-41. (Abstract Only).
Taylor et al., "Classification criteria for psoriatic arthritis: development of new criteria from a large international study", Arthritis Rheum. Aug. 2006;54(8):2665-73.
Wilson et al., "ARCHITECT® c16000™* Clinical Chemistry Analyzer Sub-System Level Performance", American Association for Clinical Chemistry Annual Meeting, Chicago, Illinois, Jul. 23-27, 2006. (4 pages).
Wirth et al., "Post-translational modification detection using metastable ions in reflector matrix-assisted laser desorption/ionization-time of flight mass spectrometry", Proteomics. Oct. 2002;2(10):1445-51.
JP 2021-009259, Office Action, dated Jan. 12, 2022, 8 pages.
Cunnane, G. et al., "Serum Amyloid A in the Assessment of Early Inflammatory Arthritis," J. Rheumatology 27(1):58-63 (2000).
Ebert, R. et al., "Acute Phase Serum Amyloid A Induces Proinflammatory Cytokines and Mineralization Via Toll-like Receptor 4 in Mesenchymal Stem Cells," Stem Cell Research 15(1):231-230 (2015).
Imai, Y. et al., "YKL-40 is a Serum Biomarker Reflecting the Severity of Cutaneous Lesions in Psoriatic Arthritis," The Journal of Dermatology 40:294-296 (2013).
Oliviero, F. et al., "A Comparative Study of Serum and Synovial Fluid Lipoprotein Levels in Patients with Various Arthritides," Clinica Chimica Acta 413(1-2):303-307 (2012).
Pedersen, S. et al., "Circulating Levels of Interleukin-6, Vascular Endothelial Growth Factor, YKL-40, Matrix Metalloproteinase-3, and Total Aggrecan in Spondyloarthritis Patients during 3 years of Treatment with TNFα Inhibitors," Clin. Rheumatol. 29(11):1301-1309 (2010).
Przepiera-Bedzak, H et al., "Serum IL-6 and IL-23 Levels and Their Correlation with Angiogenic Cytokines and Disease Activity in Ankylosing Spondylitis, Psoriatic Arthritis, and SAPHO Syndrome," Mediators of Inflammation, vol. 2015, pp. 1-7(2015).
EP 16852551.7, Office Action, dated Feb. 3, 2021, 6 pages.
CA 3,000,192, Office Action, dated Aug. 5, 2022, 4 pages.
JP 2021-009259, Notice of Decision to Grant, dated Oct. 19, 2022, 4 pages.

* cited by examiner

BIOMARKERS AND METHODS FOR ASSESSING PSORIATIC ARTHRITIS DISEASE ACTIVITY

RELATED APPLICATIONS

This application claims priority to International application number PCT/US2016/054323, filed Sep. 29, 2016, which claims priority benefit to U.S. provisional application No. 62/234,526, filed Sep. 29, 2015, the entire contents of which are hereby incorporated by reference.

BACKGROUND

This application is directed to the fields of bioinformatics and inflammatory and autoimmune diseases, with methods of assessing response to inflammatory disease therapy, in particular psoriatic arthritis (PsA) disease activity. PsA is an example of an inflammatory disease, and is a chronic, systemic autoimmune disorder, and occurs in about 30 percent of subjects having psoriasis. Psoriasis is a disease in which scaly red and white patches develop on the skin.

PsA causes pain, stiffness, and swelling in and around any joint in the body. PsA typically affects the large joints, particularly those of the lower extremities, distal joints of the fingers and toes, and also the back and sacroiliac joints of the pelvis. There are five general patterns of PsA: arthritis of the distal interphalangeal joints, destructive arthritis, symmetric polyarthritis indistinguishable from rheumatoid arthritis, asymmetric oligoarthritis, and spondyloarthropathy. Persistent inflammation from PsA can lead to joint damage.

The impact of PsA varies based on the joints affected ad the severity of symptoms. Common side effects of PsA are fatigue and anemia. Similar to psoriasis, PsA symptoms can flare and subside, and even change locations in the same subject. PsA is associated with significant morbidity and disability, and thus constitutes a major socioeconomic burden. To achieve the maximum therapeutic benefits for individual subjects, it is important to be able to specifically quantify and assess the subject's disease activity at any particular time, determine the effects of treatment on disease activity, and predict future outcomes.

SUMMARY

The present teachings relate to biomarkers associated with inflammatory disease, and with autoimmune disease, including psoriatic arthritis, and methods of using the biomarkers to measure disease activity in a subject, and in further, in response to therapy.

In one embodiment, a method for generating protein level data for a first subject is provided. The method comprises performing at least one immunoassay on a first blood sample from the first subject to generate a first dataset comprising protein level data for at least four protein markers, wherein the at least four protein markers comprise at least four markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); or, vascular endothelial growth factor A (VEGFA); and wherein the first subject has been previously diagnosed with psoriatic arthritis (PsA). In another embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In an embodiment, the at least one immunoassay comprises a multiplex assay. In an embodiment, the at least four protein markers comprise at least five markers selected from CHI3L1, CRP, EGF, IL6, LEP, MMP1, MMP3, RETN, SAA1, TNFRSF1A, VCAM1, or VEGFA. In an embodiment, the at least four protein markers comprise at least six markers selected from CHI3L1, CRP, EGF, IL6, LEP, MMP1, MMP3, RETN, SAA1, TNFRSF1A, VCAM1, or VEGFA. In an embodiment, the at least four protein markers comprise at least seven markers selected from CHI3L1, CRP, EGF, IL6, LEP, MMP1, MMP3, RETN, SAA1, TNFRSF1A, VCAM1, or VEGFA. In an embodiment, the at least four protein markers comprise at least eight markers selected from CHI3L1, CRP, EGF, IL6, LEP, MMP1, MMP3, RETN, SAA1, TNFRSF1A, VCAM1, or VEGFA. In an embodiment, the at least four protein markers comprise at least nine markers selected from CHI3L1, CRP, EGF, IL6, LEP, MMP1, MMP3, RETN, SAA1, TNFRSF1A, VCAM1, or VEGFA. In an embodiment, the at least four protein markers comprise at least ten markers selected from CHI3L1, CRP, EGF, IL6, LEP, MMP1, MMP3, RETN, SAA1, TNFRSF1A, VCAM1, or VEGFA. In an embodiment, the at least four protein markers comprise at least eleven markers selected from CHI3L1, CRP, EGF, IL6, LEP, MMP1, MMP3, RETN, SAA1, TNFRSF1A, VCAM1, or VEGFA. In an embodiment, the plurality of protein markers consists of at most 500 protein markers. In an embodiment, the plurality of protein markers consists of at most 250 protein markers. In an embodiment, the plurality of protein markers consists of at most 100 protein markers. In an embodiment, the plurality of protein markers consists of at most 50 protein markers. In an embodiment, the plurality of protein markers consists of at most 25 protein markers. In an embodiment, the plurality of protein markers consists of at most 12 protein markers. In an embodiment, the CHI3L1 is at least 90% identical to the amino acid sequence of NCBI RefSeq NP_001267.2, wherein the CRP is at least 90% identical to the amino acid sequence of NCBI RefSeq NP_000558.2, wherein the EGF is at least 90% identical to the amino acid sequence of NCBI RefSeq NP_001954.2, wherein the IL6 is at least 90% identical to the amino acid sequence of NCBI RefSeq NP_000591.1, wherein the LEP is at least 90% identical to the amino acid sequence of NCBI RefSeq NP_000221.1, wherein the MMP1 is at least 90% identical to the amino acid sequence of NCBI RefSeq NP_002412.1, wherein the MMP3 is at least 90% identical to the amino acid sequence of NCBI RefSeq NP_002413.1, wherein the RETN is at least 90% identical to the amino acid sequence of NCBI RefSeq NP_065148.1, wherein the SAA1 is at least 90% identical to the amino acid sequence of NCBI RefSeq NP_000322.2, wherein the TNFRSF1A is at least 90% identical to the amino acid sequence of NCBI RefSeq NP_001056.1, wherein the VCAM1 is at least 90% identical to the amino acid sequence of NCBI RefSeq NP_001069.1, and wherein the VEGFA is at least 90% identical to the amino acid sequence of NCBI RefSeq NP_001020539.2.

In another embodiment, a method for generating a protein level score is provided. The method comprises performing at least one immunoassay on a first blood sample from a subject previously diagnosed with psoriatic arthritis (PsA), to generate protein level data for each protein marker of a plurality of protein markers, wherein the plurality of protein markers comprises a plurality of test markers comprising at least four markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); or, vascular endothelial growth factor A (VEGFA); and combining the protein level data for each test marker to generate the protein level score. In an embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In an embodiment, the at least one immunoassay comprises a multiplex assay. In an embodiment, the at least four protein markers comprise at least five markers selected from CHI3L1, CRP, EGF, IL6, LEP, MMP1, MMP3, RETN, SAA1, TNFRSF1A, VCAM1, or VEGFA. In an embodiment, the at least four protein markers comprise at least six markers selected from CHI3L1, CRP, EGF, IL6, LEP, MMP1, MMP3, RETN, SAA1, TNFRSF1A, VCAM1, or VEGFA. In an embodiment, the at least four protein markers comprise at least seven markers selected from CHI3L1, CRP, EGF, IL6, LEP, MMP1, MMP3, RETN, SAA1, TNFRSF1A, VCAM1, or VEGFA. In an embodiment, the at least four protein markers comprise at least eight markers selected from CHI3L1, CRP, EGF, IL6, LEP, MMP1, MMP3, RETN, SAA1, TNFRSF1A, VCAM1, or VEGFA. In an embodiment, the at least four protein markers comprise at least nine markers selected from CHI3L1, CRP, EGF, IL6, LEP, MMP1, MMP3, RETN, SAA1, TNFRSF1A, VCAM1, or VEGFA. In an embodiment, the at least four protein markers comprise at least ten markers selected from CHI3L1, CRP, EGF, IL6, LEP, MMP1, MMP3, RETN, SAA1, TNFRSF1A, VCAM1, or VEGFA. In an embodiment, the at least four protein markers comprise at least eleven markers selected from CHI3L1, CRP, EGF, IL6, LEP, MMP1, MMP3, RETN, SAA1, TNFRSF1A, VCAM1, or VEGFA. In an embodiment, the plurality of test markers comprises CHI3L1, CRP, EGF, IL6, LEP, MMP1, MMP3, RETN, SAA1, TNFRSF1A, VCAM1, and VEGFA. In an embodiment, the CHI3L1 is at least 90% identical to the amino acid sequence of NCBI RefSeq NP_001267.2, wherein the CRP is at least 90% identical to the amino acid sequence of NCBI RefSeq NP_000558.2, wherein the EGF is at least 90% identical to the amino acid sequence of NCBI RefSeq NP_001954.2, wherein the IL6 is at least 90% identical to the amino acid sequence of NCBI RefSeq NP_000591.1, wherein the LEP is at least 90% identical to the amino acid sequence of NCBI RefSeq NP_000221.1, wherein the MMP1 is at least 90% identical to the amino acid sequence of NCBI RefSeq NP_002412.1, wherein the MMP3 is at least 90% identical to the amino acid sequence of NCBI RefSeq NP_002413.1, wherein the RETN is at least 90% identical to the amino acid sequence of NCBI RefSeq NP_065148.1, wherein the SAA1 is at least 90% identical to the amino acid sequence of NCBI RefSeq NP_000322.2, wherein the TNFRSF1A is at least 90% identical to the amino acid sequence of NCBI RefSeq NP_001056.1, wherein the VCAM1 is at least 90% identical to the amino acid sequence of NCBI RefSeq NP_001069.1, and wherein the VEGFA is at least 90% identical to the amino acid sequence of NCBI RefSeq NP_001020539.2.

In another embodiment, a method for providing a quantitative measure of psoriatic arthritis (PsA) disease activity in a subject previously diagnosed with PsA is provided. The method comprises providing a quantitative measure of psoriatic arthritis (PsA) disease activity in a subject previously diagnosed with PsA comprising: performing at least one immunoassay on a first sample from the subject to generate a first dataset comprising quantitative data comprising at least four markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); or, vascular endothelial growth factor A (VEGFA); and applying an algorithm to said first dataset to determine a first disease activity score, wherein said first disease activity score provides a quantitative measure of PsA disease activity in said subject. In an embodiment, the method further comprises receiving a second dataset associated with a second sample obtained from the subject, wherein the first sample and the second sample are obtained from the subject at different times; applying the algorithm to the second dataset to determine a second disease activity score; and comparing the first disease activity score and said second disease activity score to determine a change in the disease activity scores, therein the change indicates a change in the psoriatic arthritis disease activity the subject. In an embodiment, the at least four protein markers comprise at least five, six, seven, eight, nine, ten, or eleven markers selected from CHI3L1, CRP, EGF, IL6, LEP, MMP1, MMP3, RETN, SAA1, TNFRSF1A, VCAM1, or VEGFA. In an embodiment, the CHI3L1 is at least 90% identical to the amino acid sequence of NCBI RefSeq NP_001267.2, wherein the CRP is at least 90% identical to the amino acid sequence of NCBI RefSeq NP_000558.2, wherein the EGF is at least 90% identical to the amino acid sequence of NCBI RefSeq NP_001954.2, wherein the IL6 is at least 90% identical to the amino acid sequence of NCBI RefSeq NP_000591.1, wherein the LEP is at least 90% identical to the amino acid sequence of NCBI RefSeq NP_000221.1, wherein the MMP1 is at least 90% identical to the amino acid sequence of NCBI RefSeq NP_002412.1, wherein the MMP3 is at least 90% identical to the amino acid sequence of NCBI RefSeq NP_002413.1, wherein the RETN is at least 90% identical to the amino acid sequence of NCBI RefSeq NP_065148.1, wherein the SAA1 is at least 90% identical to the amino acid sequence of NCBI RefSeq NP_000322.2, wherein the TNFRSF1A is at least 90% identical to the amino acid sequence of NCBI RefSeq NP_001056.1, wherein the VCAM1 is at least 90% identical to the amino acid sequence of NCBI RefSeq NP_001069.1, and wherein the VEGFA is at least 90% identical to the amino acid sequence of NCBI RefSeq NP_001020539.2.

In another embodiment, a system for scoring a sample is provided. The system comprises a storage memory for storing a first dataset associated with a first sample obtained from a subject previously diagnosed with psoriatic arthritis (PsA), wherein said first dataset comprising quantitative data for at least four markers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); or, vascular endothelial growth factor A (VEGFA); and a processor communicatively coupled to the storage memory, the processor configured to apply an algorithm to the first dataset to determine a first disease activity score wherein said first disease activity score provides a quantitative measure of PsA disease activity in the subject and wherein the algorithm is trained using data representing the at least four markers in samples from subjects having a known PsA disease activity. In an embodiment, the at least four protein markers comprise at least five, six, seven, eight, nine, ten, or eleven markers selected from CHI3L1, CRP, EGF, IL6, LEP, MMP1, MMP3, RETN, SAA1, TNFRSF1A, VCAM1, or VEGFA. In an embodiment, the CHI3L1 is at least 90% identical to the amino acid sequence of NCBI RefSeq NP_001267.2, wherein the CRP is at least 90% identical to the amino acid sequence of NCBI RefSeq NP_000558.2, wherein the EGF is at least 90% identical to the amino acid sequence of NCBI RefSeq NP_001954.2, wherein the IL6 is at least 90% identical to the amino acid sequence of NCBI RefSeq NP_000591.1, wherein the LEP is at least 90% identical to the amino acid sequence of NCBI RefSeq NP_000221.1, wherein the MMP1 is at least 90% identical to the amino acid sequence of NCBI RefSeq NP_002412.1, wherein the MMP3 is at least 90% identical to the amino acid sequence of NCBI RefSeq NP_002413.1, wherein the RETN is at least 90% identical to the amino acid sequence of NCBI RefSeq NP_065148.1, wherein the SAA1 is at least 90% identical to the amino acid sequence of NCBI RefSeq NP_000322.2, wherein the TNFRSF1A is at least 90% identical to the amino acid sequence of NCBI RefSeq NP_001056.1, wherein the VCAM1 is at least 90% identical to the amino acid sequence of NCBI RefSeq NP_001069.1, and wherein the VEGFA is at least 90% identical to the amino acid sequence of NCBI RefSeq NP_001020539.2.

In another embodiment, a method for recommending a therapeutic regimen in a subject previously diagnosed with psoriatic arthritis (PsA) is provided. The method comprises a) performing, at a first time point, a first immunoassay on a first sample from the subject to generate a first score based on a first set of quantitative data, wherein the first set of quantitative data comprises expression data for at least four biomarkers selected from chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); or, vascular endothelial growth factor A (VEGFA); b) performing, at a second time point that is a time period after the first time point, a second immunoassay on a second sample from the subject to generate a second score based on a second set of quantitative data, wherein the second set of quantitative data comprises expression data for the at least four biomarkers; c) determining whether there is a difference between the first score and the second score; and d) recommending a therapeutic regimen, or modifying an existing therapeutic regimen, based on the difference between the first and second scores. In an embodiment, a non-biologic therapeutic regimen is recommended if the difference between the first and second scores indicate a reduction or no change in PsA disease activity. In an embodiment, a biologic therapeutic regimen is recommended if the difference between the first and second scores indicate an increase in PsA disease activity. In an embodiment, performance of the at least one immunoassay comprises: obtaining the first sample, wherein the first sample comprises the protein markers; contacting the first sample with a plurality of distinct reagents; generating a plurality of distinct complexes between the reagents and markers; and detecting the complexes to generate the data. In an embodiment, the first and second immunoassays comprise a multiplex assay. In an embodiment, the at least four protein markers comprise at least five, six, seven, eight, nine, ten, or eleven markers selected from CHI3L1, CRP, EGF, IL6, LEP, MMP1, MMP3, RETN, SAA1, TNFRSF1A, VCAM1, or VEGFA. In an embodiment, the CHI3L1 is at least 90% identical to the amino acid sequence of NCBI RefSeq NP_001267.2, wherein the CRP is at least 90% identical to the amino acid sequence of NCBI RefSeq NP_000558.2, wherein the EGF is at least 90% identical to the amino acid sequence of NCBI RefSeq NP_001954.2, wherein the IL6 is at least 90% identical to the amino acid sequence of NCBI RefSeq NP_000591.1, wherein the LEP is at least 90% identical to the amino acid sequence of NCBI RefSeq NP_000221.1, wherein the MMP1 is at least 90% identical to the amino acid sequence of NCBI RefSeq NP_002412.1, wherein the MMP3 is at least 90% identical to the amino acid sequence of NCBI RefSeq NP_002413.1, wherein the RETN is at least 90% identical to the amino acid sequence of NCBI RefSeq NP_065148.1, wherein the SAA1 is at least 90% identical to the amino acid sequence of NCBI RefSeq NP_000322.2, wherein the TNFRSF1A is at least 90% identical to the amino acid sequence of NCBI RefSeq NP_001056.1, wherein the VCAM1 is at least 90% identical to the amino acid sequence of NCBI RefSeq NP_001069.1, and wherein the VEGFA is at least 90% identical to the amino acid sequence of NCBI RefSeq NP_001020539.2.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Figure 1:
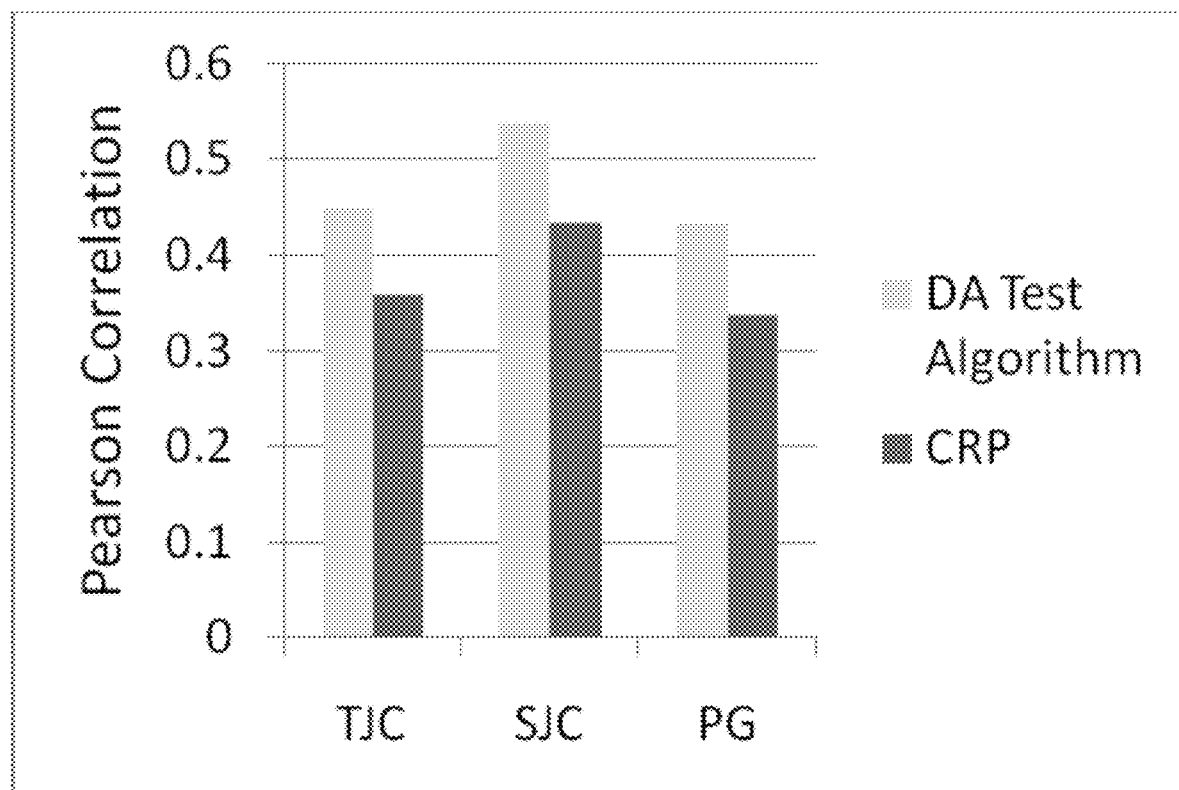
FIG. 1 depicts correlations of the MBDA algorithm predictions and CRP with clinical assessments of disease activity, as described in Example 1.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to the identification of biomarkers associated with subjects having inflammatory and/or autoimmune diseases, for example, psoriatic arthritis (PsA), and are useful in determining or assessing disease activity.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other and/or equivalent terms for "accuracy" can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, Circulation 2006, 113(19):2335-2362 for a summary of considerations in evaluating new biomarkers.

The term "administering" as used herein refers to the placement of a composition into a subject by a method or route that results in at least partial localization of the composition at a desired site such that a desired effect is produced. Routes of administration include both local and systemic administration. Generally, local administration results in more of the composition being delivered to a specific location as compared to the entire body of the subject, whereas, systemic administration results in delivery to essentially the entire body of the subject.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's disease activity.

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., APOA1 as used herein can refer to the gene APOA1 and also the protein ApoA1. In general, hyphens are dropped from analyte names and symbols herein (IL-6=IL6).

To "analyze" includes determining a value or set of values associated with a sample by measurement of analyte levels in the sample. "Analyze" may further comprise comparing the levels against constituent levels in a sample or set of samples from the same subject or other subject(s). The biomarkers of the present teachings can be analyzed by any of various conventional methods known in the art. Some such methods include but are not limited to: measuring serum protein or sugar or metabolite or other analyte level, measuring enzymatic activity, and measuring gene expression.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, early rheumatoid arthritis (RA), axial spondyloarthritis, juvenile idiopathic arthritis, seronegative spondyloarthropathies, ankylosing spondylitis, psoriatic arthritis (PsA), antiphospholipid antibody syndrome, autoimmune hepatitis, Behcet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis *nodosa*, Churg-Strauss Syndrome, and mixed cryoglobulinemic vasculitis.

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences. Biomarkers can include, but are not limited to, apolipoprotein A-I (APOA1); apolipoprotein C-III (APOC3); calprotectin; chemokine (C-C motif) ligand 22 (CCL22); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); ICTP; interleukin 18 (interferon-gamma-inducing factor) (IL18); interleukin 1, beta (IL1B); interleukin 6 receptor (IL6R); interleukin 8 (IL8); keratan sulfate, or KS; leptin (LEP); matrix metallopeptidase 1 (interstitial collagenase) (MMP1); matrix metallopeptidase 3 (stromelysin 1, progelatinase) (MMP3); pyridinoline (cross-links formed in collagen, derived from three lysine residues), which may be referred to herein as PYD; resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA).

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for RA, as an example, can comprise, without limitation, one or more of the following: DAS, DAS28, DAS28-ESR, DAS28-CRP, HAQ, mHAQ, MDHAQ, physician global assessment VAS, patient global assessment VAS, pain VAS, fatigue VAS, overall VAS, sleep VAS, SDAI, CDAI, RAPID3, RAPID4, RAPID5, ACR20, ACR50, ACR70, SF-36 (a well-validated measure of general health status), RA MM score (RAIVIRIS; or RA Mill scoring system), total Sharp score (TSS), van der Heijde-modified TSS, van der Heijde-modified Sharp score (or Sharp-van der Heij de score (SHS)), Larsen score, TJC, swollen joint count (SJC), CRP titer (or level), and ESR. One of skill in the art will recognize that the clinical assessment for PsA, as an example, can also comprise, without limitation, one or more of the following: physician global assessment, HAQ score, skin BSA, and CDAI.

The term "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to DMARDs, whether conventional or biologics, steroids, etc.), TJC, SJC, morning stiffness, arthritis of three or more joint areas, arthritis of hand joints, psoriasis, symmetric arthritis, rheumatoid nodules, radiographic changes and other imaging, gender/sex, age, race/ethnicity, disease duration, diastolic and systolic blood pressure, resting heart rate, height, weight, body-mass index, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP titer can be used as a clinical assessment of disease activity; or, it can be used as a measure of the health status of a subject, and thus serve as a clinical parameter.

Figure 3:
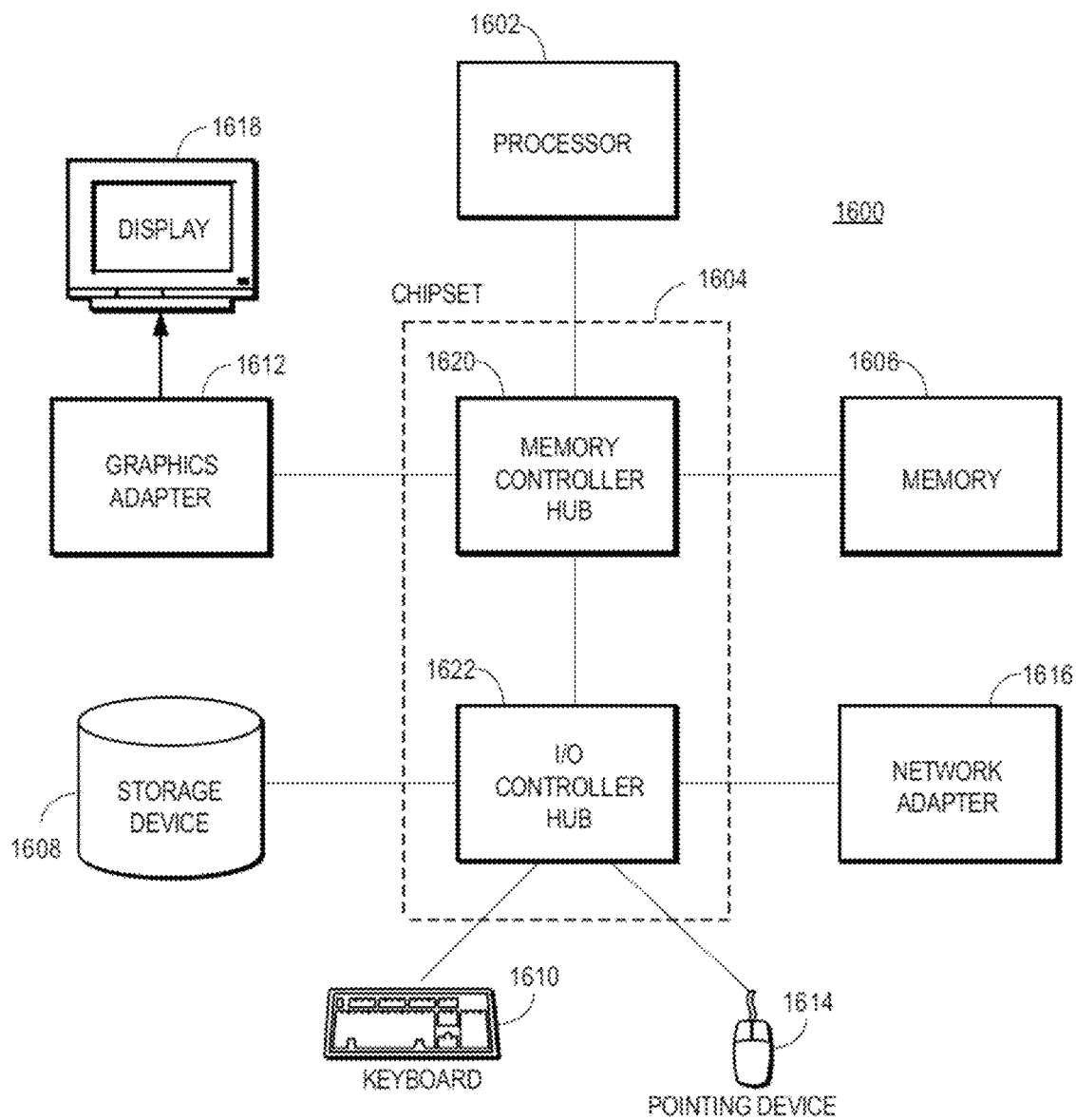
FIG. 3 illustrates a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.

The term "computer" carries the meaning that is generally known in the art; that is, a machine for manipulating data according to a set of instructions. For illustration purposes only, FIG. 3 is a high-level block diagram of a computer (1600). As is known in the art, a "computer" can have different and/or other components than those shown in FIG. 3. In addition, the computer 1600 can lack certain illustrated components. Moreover, the storage device (1608) can be local and/or remote from the computer (1600) (such as embodied within a storage area network (SAN)). As is known in the art, the computer (1600) is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells of the immune system that carries signals locally between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

"DAS" refers to the Disease Activity Score, a measure of the activity of RA in a subject, well-known to those of skill in the art. See D. van der Heijde et al., *Ann. Rheum. Dis.* 1990, 49(11):916-920. "DAS" as used herein refers to this particular Disease Activity Score. The "DAS28" involves the evaluation of 28 specific joints. It is a current standard well-recognized in research and clinical practice. Because the DAS28 is a well-recognized standard, it is often simply referred to as "DAS." Unless otherwise specified, "DAS" herein will encompass the DAS28. A DAS28 can be calculated for an RA subject according to the standard as outlined at the das-score.nl website, maintained by the Department of Rheumatology of the University Medical Centre in Nijmegen, the Netherlands. The number of swollen joints, or swollen joint count out of a total of 28 (SJC28), and tender joints, or tender joint count out of a total of 28 (TJC28) in each subject is assessed. In some DAS28 calculations the subject's general health (GH) is also a factor, and can be measured on a 100 mm Visual Analogue Scale (VAS). GH may also be referred to herein as PG or PGA, for "patient global health assessment" (or merely "patient global assessment"). A "patient global health assessment VAS," then, is GH measured on a Visual Analogue Scale.

"DAS28-CRP" (or "DAS28CRP") is a DAS28 assessment calculated using CRP in place of ESR (see below). CRP is produced in the liver. Normally there is little or no CRP circulating in an individual's blood serum—CRP is generally present in the body during episodes of acute inflammation or infection, so that a high or increasing amount of CRP in blood serum can be associated with acute infection or inflammation. A blood serum level of CRP greater than 1 mg/dL is usually considered high. Most inflammation and infections result in CRP levels greater than 10 mg/dL. The amount of CRP in subject sera can be quantified using, for example, the DSL-10-42100 ACTIVE® US C-Reactive Protein Enzyme-Linked Immunosorbent Assay (ELISA), developed by Diagnostics Systems Laboratories, Inc. (Webster, Tex.). CRP production is associated with radiological progression in RA. See M. Van Leeuwen et al., *Br. J. Rheum.* 1993, 32(suppl.):9-13). CRP is thus considered an appropriate alternative to ESR in measuring RA disease activity. See R. *Mallya* et al., *J. Rheum.* 1982, 9(2):224-228, and F. Wolfe, *J. Rheum.* 1997, 24:1477-1485.

The DAS28-CRP can be calculated according to either of the formulas below, with or without the GH factor, where "CRP" represents the amount of this protein present in a subject's blood serum in mg/L, "sqrt" represents the square root, and "ln" represents the natural logarithm:

*DAS*28-CRP with GH(or *DAS*28-CRP4)=(0.56*sqrt (TJC28)+0.28*sqrt(SJC28)+0.36*ln(CRP+1))+ (0.014*GH)+0.96; or, (a)

*DAS*28-CRP without GH(or *DAS*28-CRP3)= (0.56*sqrt(TJC28)+0.28*sqrt(SJC28)+0.36*ln (CRP+1))*1.10+1.15. (b)

The "DAS28-ESR" is a DAS28 assessment wherein the ESR for each subject is also measured (in mm/hour). The DAS28-ESR can be calculated according to the formula:

*DAS*28-*ESR* with GH(or *DAS*28-*ESR*4)=0.56*sqrt (TJC28)+0.28*sqrt(SJC28)+0.70*ln(*ESR*)+ 0.014*GH; or, (a)

*DAS*28-*ESR* without GH=0.56*sqrt(TJC28)+ 0.28*sqrt(SJC28)+0.70*ln(*ESR*)*1.08+0.16. (b)

Unless otherwise specified herein, the term "DAS28," as used in the present teachings, can refer to a DAS28-ESR or DAS28-CRP, as obtained by any of the four formulas described above; or, DAS28 can refer to another reliable DAS28 formula as may be known in the art.

A "dataset" or "data" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

A "difference" as used herein refers to an increase or decrease in the measurable expression of a biomarker or panel of biomarkers as compared to the measurable expression of the same biomarker or panel of biomarkers in a second samples.

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A DMARD can be conventional or biologic. Examples of DMARDs that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Examples of other conventional DMARDs include, but are not limited to, folinic acid, D-pencillamine, gold auranofin, gold aurothioglucose, gold thiomalate, cyclophosphamide, and chlorambucil. Examples of biologic DMARDs (or biologic drugs) include but are not limited to biological agents that target the tumor necrosis factor (TNF)-alpha molecules and the TNF inhibitors, such as infliximab, adalimumab, etanercept and golimumab. Other classes of biologic DMARDs include IL1 inhibitors such as anakinra, T-cell modulators such as abatacept, B-cell modulators such as rituximab, and IL6 inhibitors such as tocilizumab.

An "immunoassay" as used herein refers to a biochemical assay that uses one or more antibodies to measure the presence or concentration of an analyte or biomarker in a biological sample. A "multiplex immunoassay" as used herein refers to a biochemical assay that uses more than one antibody to simultaneously measure multiple analytes in a single run/cycle of the assay.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Non-limiting examples of inflammatory disease include RA, ankylosing spondylitis, psoriatic arthritis, psoriasis, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity or the disease state of a subject.

"Measuring" or "measurement" in the context of the present teachings refers to determining the presence, absence, quantity, amount, or effective amount of a substance in a clinical or subject-derived sample, including the concentration levels of such substances, or evaluating the values or categorization of a subject's clinical parameters.

"Performance" in the context of the present teachings relates to the quality and overall usefulness of, e.g., a model, algorithm, or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test. Performing can mean the act of carrying out a function.

A "population" is any grouping of subjects of like specified characteristics. The grouping could be according to, for example but without limitation, clinical parameters, clinical assessments, therapeutic regimen, disease status (e.g. with disease or healthy), level of disease activity, etc. In the context of using the MBDA score in comparing disease activity between populations, an aggregate value can be determined based on the observed MBDA scores of the subjects of a population; e.g., at particular timepoints in a longitudinal study. The aggregate value can be based on, e.g., any mathematical or statistical formula useful and known in the art for arriving at a meaningful aggregate value from a collection of individual datapoints; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a datapoint without actually performing the clinical diagnostic procedures normally or otherwise required to produce that datapoint; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of disease activity or the disease state of a subject. See Calculation of the MBDA score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset" or "quantitative data" as used in the present teachings, refers to the data derived from, e.g., detection and composite measurements of expression of a plurality of biomarkers (i.e., two or more) in a subject sample. The quantitative dataset can be used to generate a score for the identification, monitoring and treatment of disease states, and in characterizing the biological condition of a subject. It is possible that different biomarkers will be detected depending on the disease state or physiological condition of interest.

"Recommending" as used herein refers to making a recommendation for a therapeutic regimen or excluding (i.e., not recommending) a certain therapeutic regimen for a subject. Such a recommendation shall serve optionally together with other information as a basis for a clinician to apply a certain therapeutic regimen for an individual subject.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "score" is a value or set of values selected so as to provide a quantitative measure of a variable or characteristic of a subject's condition, and/or to discriminate, differentiate or otherwise characterize a subject's condition. The value(s) comprising the score can be based on, for example, quantitative data resulting in a measured amount of one or more sample constituents obtained from the subject, or from clinical parameters, or from clinical assessments, or any combination thereof. In certain embodiments the score can be derived from a single constituent, parameter or assessment, while in other embodiments the score is derived from multiple constituents, parameters and/or assessments. The score can be based upon or derived from an interpretation function; e.g., an interpretation function derived from a particular predictive model using any of various statistical algorithms known in the art. A "change in score" can refer to the absolute change in score, e.g. from one time point to the next, or the percent change in score, or the change in the score per unit time (i.e., the rate of score change). A "score" as used herein can be used interchangeably with MBDA score as defined below.

A "multi-biomarker disease activity index score," "MBDA score," or simply "MBDA," in the context of the present teachings, is a score that uses quantitative data to provide a quantitative measure of inflammatory disease activity or the state of inflammatory disease in a subject. A set of data from particularly selected biomarkers, such as from the disclosed set of biomarkers, is input into an interpretation function according to the present teachings to derive the MBDA score. The interpretation function, in some embodiments, can be created from predictive or multivariate modeling based on statistical algorithms. Input to the interpretation function can comprise the results of testing two or more of the disclosed set of biomarkers, alone or in combination with clinical parameters and/or clinical assessments, also described herein. In some embodiments of the present teachings, the MBDA score is a quantitative measure of autoimmune disease activity. In some embodiments, the MBDA score is a quantitative measure of RA disease activity. In some embodiments, the MBDA score is a quantitative measure of PsA disease activity. MBDA as used herein can refer to a VECTRA® DA score.

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease such as PsA. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional DMARDs, biologic DMARDs, non-steroidal anti-inflammatory drugs (NSAID's) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen.

A "time point" as used herein refers to a manner of describing a time, which can be substantially described with a single point. A time point may also be described as a time range of a minimal unit which can be detected. A time point can refer to a state of the aspect of a time or a manner of description of a certain period of time. Such a time point or range can include, for example, an order of seconds, minutes to hours, or days.

Use of the Present Teachings in the Assessment of Disease Activity

In some embodiments of the present teachings, biomarkers can be used in the derivation of a MBDA score, as described herein, which MBDA score can be used to assess disease state and/or disease activity in inflammatory disease and in autoimmune disease, in particular RA or PsA. In certain embodiments, the MBDA score can be used to assess disease state and/or disease activity of PsA in response to therapy.

Identifying the state of inflammatory disease in a subject allows for a prognosis of the disease, and thus for the informed selection of, initiation of, adjustment of or increasing or decreasing various therapeutic regimens in order to delay, reduce or prevent that subject's progression to a more advanced disease state. In some embodiments, therefore, subjects can be identified as having a particular level of inflammatory disease activity and/or as being at a particular state of disease, based on the determination of their MBDA scores, and so can be selected to begin or accelerate treatment, as treatment is defined herein, to prevent or delay the further progression of inflammatory disease. In other embodiments, subjects that are identified via their MBDA scores as having a particular level of inflammatory disease activity, and/or as being at a particular state of inflammatory disease, can be selected to have their treatment decreased or discontinued, where improvement or remission in the subject is seen.

Rating Disease Activity

In some embodiments of the present teachings, the MBDA score, derived as described herein, can be used to rate inflammatory disease activity; e.g., as high, medium or low. The score can be varied based on a set of values chosen by the practitioner. For example, a score can be set such that a value is given a range from 0-100, and a difference between two scores would be a value of at least one point. The practitioner can then assign disease activity based on the values. For example, in some embodiments a score of 1 to 29 represents a low level of disease activity, a score of 30 to 44 represents a moderate level of disease activity, and a score of 45 to 100 represents a high level of disease activity. The disease activity score can change based on the range of the score. For example a score of 1 to 58 can represent a low level of disease activity when a range of 0-200 is utilized. Differences can be determined based on the range of score possibilities. For example, if using a score range of 0-100, a small difference in scores can be a difference of about 1, 2, 3, 4, 5, 6, 7, 8, 9, or 10 points; a moderate difference in scores can be a difference of about 4, 5, 6, 7, 8, 9, 10, 11, 12, 13, 14, 15, 16, 17, 18, 19, 20, 21, 22, 23, 24, 25, 26, 27, 28, 29, or 30 points; and large differences can be a change in about 14, 15, 16, 17, 18, 19, 20, 21, 22, 23, 24, 25, 26, 27, 28, 29, 30, 35, 40, 45, or 50 points. Thus, by way of example, a practitioner can define a small difference in scores as about ≤6 points, a moderate difference in scores as about 7-20 points, and a large difference in scores as about >20 points. The difference can be expressed by any unit, for example, percentage points. For example, a practitioner can define a small difference as about ≤6 percentage points, moderate difference as about 7-20 percentage points, and a large difference as about >20 percentage points.

In some embodiments of the present teachings, autoimmune disease activity can be so rated. In other embodiments, RA disease activity can be so rated. In other embodiments, PsA disease activity can be so rated. Because the MBDA score correlates well with traditional clinical assessments of inflammatory disease activity, e.g. in PsA, in other embodiments of the present teachings bone damage itself in a subject or population, and thus disease progression, can be tracked via the use and application of the MBDA score.

The MBDA score can be used for several purposes. On a subject-specific basis, it provides a context for understanding the relative level of disease activity. The MBDA rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness. Because the MBDA score demonstrates strong association with established disease activity assessments, such as the DAS28, the MBDA score can provide a quantitative measure for monitoring the extent of subject disease activity, and response to treatment.

Subject Screening

Certain embodiments of the present teachings can also be used to screen subject populations in any number of settings. For example, a health maintenance organization, public health entity or school health program can screen a group of subjects to identify those requiring interventions, as described above. Other embodiments of these teachings can be used to collect disease activity data on one or more populations of subjects, to identify subject disease status in the aggregate, in order to, e.g., determine the effectiveness of the clinical management of a population, or determine gaps in clinical management. Insurance companies (e.g., health, life, or disability) may request the screening of applicants in the process of determining coverage for possible intervention. Data collected in such population screens, particularly when tied to any clinical progression to conditions such as RA or PsA, will be of value in the operations of, for example, health maintenance organizations, public health programs and insurance companies.

Such data arrays or collections can be stored in machine-readable media and used in any number of health-related data management systems to provide improved healthcare services, cost-effective healthcare, and improved insurance operation, among other things. See, e.g., U.S. Patent Application No. 2002/0038227; U.S. Patent Application No. 2004/0122296; U.S. Patent Application No. 2004/0122297; and U.S. Pat. No. 5,018,067. Such systems can access the data directly from internal data storage or remotely from one or more data storage sites as further detailed herein. Thus, in a health-related data management system, wherein it is important to manage inflammatory disease progression for a population in order to reduce disease-related employment productivity loss, disability and surgery, and thus reduce healthcare costs in the aggregate, various embodiments of the present teachings provide an improvement comprising the use of a data array encompassing the biomarker measurements as defined herein, and/or the resulting evaluation of disease status and activity from those biomarker measurements.

Calculation of Scores

In some embodiments of the present teachings, inflammatory disease activity in a subject is measured by: determining the levels in inflammatory disease subject serum of two or more biomarkers, then applying an interpretation function to transform the biomarker levels into a single MBDA score, which provides a quantitative measure of inflammatory disease activity in the subject, correlating well with traditional clinical assessments of inflammatory disease activity (e.g., a DAS28 or CDAI score in RA or PsA), as is demonstrated in the Examples below. In some embodiments, the disease activity so measured relates to an autoimmune disease. In some embodiments, the disease activity so measured relates to RA. In some embodiments, the disease activity so measured relates to PsA. The biomarkers can include apolipoprotein A-I (APOA1); apolipoprotein C-III (APOC3); calprotectin; chemokine (C-C motif) ligand 22 (CCL22); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); ICTP; interleukin 18 (interferon-gamma-inducing factor) (IL18); interleukin 1, beta (IL1B); interleukin 6 receptor (IL6R); interleukin 8 (IL8); keratan sulfate, or KS; leptin (LEP); matrix metallopeptidase 1 (interstitial collagenase) (MMP1); matrix metallopeptidase 3 (stromelysin 1, progelatinase) (MMP3); pyridinoline (cross-links formed in collagen, derived from three lysine residues), which may be referred to herein as PYD; resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA). Selection of the biomarkers of the present invention is described in detail in US 2011/0137851. Calprotectin is a heteropolymer, comprising two protein subunits of gene symbols S100A8 and S100A9. ICTP is the carboxyterminal telopeptide region of type I collagen, and is liberated during the degradation of mature type I collagen. Type I collagen is present as fibers in tissue; in bone, the type I collagen molecules are crosslinked. The ICTP peptide is immunochemically intact in blood. (For the type I collagen gene, see official symbol COL1A1, HUGO Gene Nomenclature Committee; also known as 014; alpha 1 type I collagen; collagen alpha 1 chain type I; collagen of skin, tendon and bone, alpha-1 chain; and, pro-alpha-1 collagen type 1). Keratan sulfate (KS, or keratosulfate) is not the product of a discrete gene, but refers to any of several sulfated glycosaminoglycans. They are synthesized in the central nervous system, and are found especially in cartilage and bone. Keratan sulfates are large, highly hydrated molecules, which in joints can act as a cushion to absorb mechanical shock. In some embodiments, the biomarkers can comprise two, or three, or four, or five, or six, or seven, or eight, or nine, or ten, or eleven, or twelve of IL6, EGF, VEGFA, LEP, SAA1, VCAM1, CRP, MMP1, MMP3, TNFRSF1A, RETN, and CHI3L1. In some embodiments, the biomarkers can comprise as least four biomarkers that comprise IL6, EGF, SAA1, and CRP.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides easily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are easily interpretable—one follows a series of if/then tree branches until a classification results.

Support vector machines (SVM) classify objects into two or more classes. Examples of classes include sets of treatment alternatives or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=$(y_{kj})$ with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

One example of an interpretation function that provides a MBDA score, derived from a statistical modeling method as described above, is given by the following function:

$$MBDA = b_0 + b_1 * DAIMRK_1^x - b_2 * DAIMRK_2^x - b_3 * DAIMRK_3^x \ldots - b_n * DAIMRK_n^x;$$

where MBDA is the MBDA score, $b_{0-n}$ are constants, and $DAIMRK_{1-n}^x$ are the serum concentrations to the $x^{th}$ power of n different biomarkers selected from the biomarkers disclosed herein. MBDA scores thus obtained for RA subjects with known clinical assessments (e.g., DAS28 scores) can then be compared to those known assessments to determine the level of correlation between the two assessments, and hence determine the accuracy of the MBDA score and its underlying predictive model. See Examples below for specific formulas and constants.

More generally, the function can be described as:
$MBDA = F(DAIMRK_1^x, DAIMRK_2^x, DAIMRK_n^x)$ where MBDA is the MBDA score, F is the function, and $DAIMRK_{1-n}^x$ are the serum concentrations to the $x^{th}$ power of n different biomarkers selected from the biomarkers disclosed herein. The function is described in the following paragraph.

An interpretation function for providing a MBDA score can also be derived based on models built to predict components of a disease activity assessment, such as DAS28-CRP, rather than predicting disease activity entirely. See Example 1. An example of such a function is given by the following, wherein biomarkers are used to provide improved predicted components of the DAS score:

$$MBDA\ score = ((0.56*sqrt(IPTJC)) + (0.28*sqrt(IPSJC)) + (0.14*PPGA) + (0.36*\ln(CRP/10^6 + 1)) + 0.96)*10.53 + 1;$$

IPTJC=Improved PTJC=max(0.1739*PTJC+ 0.7865*PSJC,0);

IPSJC=Improved PSJC=max(0.1734*PTJC+ 0.7839*PSJC,0);

PTJC=Prediction of Tender Joint Count=−38.564+ 3.997*(SAA1)$^{1/10}$+17.331*(IL6)$^{1/10}$+4.665*(CHI3L1)$^{1/10}$−15.236*(EGF)$^{1/10}$+2.651*(TNFRSF1A)$^{1/10}$+2.641*(LEP)$^{1/10}$+4.026*(VEGFA)$^{1/10}$−1.47*(VCAM1)$^{1/10}$;

PSJC=Prediction of Swollen Joint Count=−25.444+ 4.051*(SAA1)$^{1/10}$+16.154*(IL6)$^{1/10}$−11.847*(EGF)$^{1/10}$+3.091*(CHI3L1)$^{1/10}$+0.353*(TNFRSF1A)$^{1/10}$;

PPGA=Prediction of Patient Global Assessment=− 13.489+5.474*(IL6)$^{1/10}$+0.486*(SAA1)$^{1/10}$+ 2.246*(MMP1)$^{1/10}$+1.684*(leptin)$^{1/10}$+4.14*(TNFRSF1A)$^{1/10}$+2.292*(VEGFA)$^{1/10}$−1.898*(EGF)$^{1/10}$+0.028*(MMP3)$^{1/10}$−2.892*(VCAM1)$^{1/10}$−0.506*(RETN)$^{1/10}$ in which serum levels x for all biomarkers but CRP are transformed as $x^{1/10}$ units for all biomarkers are in pg/mL, and ln is natural log, or $\log_e$.

Where CRP units are obtained in mg/L and other markers are pg/mL, MBDA score=((0.56*sqrt(IPTJC))+(0.28*sqrt(IPSJC))+(0.14*(PPGA))+(0.36*ln(CRP+1))+0.96)*10.53+1.

The MBDA score can be further rounded and capped, in order to provide a whole number between 1 and 100, the scaled MBDA score. To accomplish this, the immediately preceding function can be re-written:
scaled MBDA score=round(max(min((0.56*sqrt(IPTJC)+ (0.28*sqrt(IPSJC))+(0.14*(PPGA))+(0.36*ln(CRP+1)+ 0.96)*10.53+1, 100),1)). Biomarker gene names provided in the above formulas represent the concentrations of those markers, and will depend on the types of assays used.

In some embodiments of the present teachings, it is not required that the MBDA score be compared to any predetermined "reference," "normal," "control," "standard," "healthy," "pre-disease" or other like index, in order for the MBDA score to provide a quantitative measure of inflammatory disease activity in the subject.

In other embodiments of the present teachings, the amount of the biomarker(s) can be measured in a sample and used to derive a MBDA score, which MBDA score is then compared to a "normal" or "control" level or value, utilizing techniques such as, e.g., reference or discrimination limits or risk defining thresholds, in order to define cut-off points and/or abnormal values for inflammatory disease. The normal level then is the level of one or more biomarkers or combined biomarker indices typically found in a subject who is not suffering from the inflammatory disease under evaluation. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose inflammatory disease activity level or state is known. In some embodiments of the present teachings, the reference value can be derived from one or more subjects who have been exposed to treatment for inflammatory disease, or from one or more subjects who are at low risk of developing inflammatory disease, or from subjects who have shown improvements in inflammatory disease activity factors (such as, e.g., clinical parameters as defined herein) as a result of exposure to treatment. In some embodiments the reference value can be derived from one or more subjects who have not been exposed to treatment; for example, samples can be collected from (a) subjects who have received initial treatment for inflammatory disease, and (b) subjects who have received subsequent treatment for inflammatory disease, to monitor the progress of the treatment. A reference value can also be derived from disease activity algorithms or computed indices from population studies.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server. Biomarker levels can be measured using any of several techniques known in the art. The present teachings encompass such techniques, and further include all subject fasting and/or temporal-based sampling procedures for measuring biomarkers.

The actual measurement of levels of the biomarkers can be determined at the protein or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the public database entries for the biomarker, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker is detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. Immunoassays carried out in accordance with the present teachings can be multiplexed. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727,022 to C. Skold et al., titled "Novel Methods for Modulating Ligand-Receptor Interactions and their Application"; U.S. Pat. No. 4,659,678 to G C Forrest et al., titled "Immunoassay of Antigens"; U.S. Pat. No. 4,376,110 to GS David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for an assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

Therapeutic Regimens

The present invention provides methods of recommending therapeutic regimens following the determination of differences in expression of the biomarkers disclosed herein. Measuring scores derived from expression levels of the biomarkers disclosed herein over a period time can provide a clinician with a dynamic picture of a subject's biological state. These embodiments of the present teachings thus will provide subject-specific biological information, which will be informative for therapy decision and will facilitate therapy response monitoring, and should result in more rapid and more optimized treatment, better control of disease activity, and an increase in the proportion of subjects achieving remission.

Treatment strategies for autoimmune disorders are confounded by the fact that some autoimmune disorders, such as PsA, is a classification given to a group of subjects with a diverse array of related symptoms. This suggests that certain subtypes of PsA are driven by specific cell type or cytokine. As a likely consequence, no single therapy has proven optimal for treatment. Given the increasing numbers of therapeutic options available for PsA, the need for an individually tailored treatment directed by immunological prognostic factors of treatment outcome is imperative. In various embodiments of the present teachings, a biomarker-derived algorithm can be used to quantify therapy response in PsA subjects. Identification of patients with a higher likelihood of responding to any given therapy would lead to more personalized medicine and increased effectiveness of therapy, which is an objective of this invention.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. Expression levels of the one or more biomarkers can be combined into a score, which can represent disease activity. The reference standard used for any embodiment disclosed herein may comprise average, mean, or median levels of the one or more analyte biomarkers or the levels of the specific panel of analyte biomarkers in a control population. The reference standard may further include an earlier time point for the same subject. For example, a reference standard may include a first time point, and the levels of the one or more analyte biomarkers can be examined again at second, third, fourth, fifth, sixth time points, etc. Any time point earlier than any particular time point can be considered a reference standard. The reference standard may additionally comprise cutoff values or any other statistical attribute of the control population, or earlier time points of the same subject, such as a standard deviation from the mean levels of the one or more analyte biomarkers or the levels of the specific panel of analyte biomarkers. In some embodiments, the control population may comprise healthy individuals or the same subject prior to the administration of any therapy.

In some embodiments, a score may be obtained from the reference time point, and a different score may be obtained from a later time point. A first time point can be when an initial therapeutic regimen is begun. A first time point can also be when a first immunoassay is performed. A time point can be hours, days, months, years, etc. In some embodiments, a time point is one month. In some embodiments, a time point is two months. In some embodiments, a time point is three months. In some embodiments, a time point is four months. In some embodiments, a time point is five months. In some embodiments, a time point is six months. In some embodiments, a time point is seven months. In some embodiments, a time point is eight months. In some embodiments, a time point is nine months. In some embodiments, a time point is ten months. In some embodiments, a time point is eleven months. In some embodiments, a time point is twelve months. In some embodiments, a time point is two years. In some embodiments, a time point is three years. In some embodiments, a time point is four years. In some embodiments, a time point is five years. In some embodiments, a time point is ten years.

A difference in the score can be interpreted as a decrease in disease activity. For example, lower score can indicate a lower level of disease activity. In these circumstances a second score having a lower score than the reference score, or first score, means that the subject's disease activity has been lowered (improved) between the first and second time periods. Alternatively, a higher score can indicate a lower level of disease activity. In these circumstances, a second score having a higher score than the reference score, or first score, also means that the subject's disease activity has improved between the first and second time periods.

A difference in the score can also be interpreted as an increase in disease activity. For example, lower score can indicate a higher level of disease activity. In these circumstances a second score having a lower score than the reference score, or first score, means that the subject's disease activity has been increased (worsened) between the first and second time periods. Alternatively, a higher score can indicate a higher level of disease activity. In these circumstances, a second score having a higher score than the reference score, or first score, also means that the subject's disease activity has worsened between the first and second time periods.

The differences can be variable. For example, when a difference in the score is interpreted as a decrease in disease activity, a large difference can mean a greater decrease in disease activity than a lower or moderate difference. Alternatively, when a difference in the score is interpreted as an increase in disease activity, a large difference can mean a greater increase in disease activity than a lower or moderate difference.

Reference Therapy for Treatment

In some embodiments, a patient is treated more or less aggressively than a reference therapy based on the difference of scores. A reference therapy is any therapy that is the standard of care for the autoimmune disorder. The standard of care can vary temporally and geographically, and a skilled person can easily determine the appropriate standard of care by consulting the relevant medical literature.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Autoimmune Disorders

In one embodiment, the practitioner adjusts the therapy based on a comparison between difference scores. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Therapies can be conventional or biologic. Examples of therapies, such as disease modifying anti-rheumatic drugs (DMARD) that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Conventional therapies can also include nonsteroidal anti-inflammatory drugs (NDAIDs), such as aspirin, ibuprofen, oxaprozin, prioxicam, indomethacin, etodolac, meclofenamate, meloxicam, naproxen, ketoprofen, nabumetorne, tolmetin sodium, and diclofenac. Examples of other conventional therapies include, but are not limited to, folinic acid, D-pencillamine, gold auranofin, gold aurothioglucose, gold thiomalate, cyclophosphamide, and chlorambucil. Examples of biologic drugs can include but are not limited to biological agents that target the tumor necrosis factor (TNF)-alpha molecules and the TNF inhibitors, such as infliximab, adalimumab, etanercept and golimumab. Other classes of biologic drugs include IL1 inhibitors such as anakinra, T-cell modulators such as abatacept, B-cell modulators such as rituximab, and IL6 inhibitors such as tocilizumab.

To identify additional therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in inflammatory disease state or activity (e.g., clinical parameters or traditional laboratory risk factors) as a result of such treatment or exposure.

Clinical Assessments of the Present Teachings

In some embodiments of the present teachings, MBDA scores are tailored to the population, endpoints or clinical assessment, and/or use that is intended. For example, a MBDA score can be used to assess subjects for primary prevention, and for secondary prevention and management. For the primary assessment, the MBDA score can be used for prediction and risk stratification for future conditions or disease sequelae, for the prognosis of disease activity and rate of change, and for indications for future therapeutic regimens. For secondary prevention and clinical management, the MBDA score can be used for prognosis and risk stratification. The MBDA score can be used for clinical decision support, such as determining whether to defer intervention or treatment, to recommend preventive check-ups for at-risk patients, to recommend increased visit frequency, to recommend increased testing, and to recommend intervention. The MBDA score can also be useful for therapeutic selection, determining response to treatment, adjustment and dosing of treatment, monitoring ongoing therapeutic efficiency, and indication for change in therapeutic regimen.

Systems for Implementing Disease Activity Tests

Tests for measuring disease activity according to various embodiments of the present teachings can be implemented on a variety of systems typically used for obtaining test results, such as results from immunological or nucleic acid detection assays. Such systems may comprise modules that automate sample preparation, that automate testing such as measuring biomarker levels, that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems are typically designed such that they also comprise modules to collect, store, and track results, such as by connecting to and utilizing a database residing on hardware. Examples of these modules include physical and electronic data storage devices as are well-known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention comprises a system for determining the inflammatory disease activity of a subject. In some embodiments, the system employs a module for applying a formula to an input comprising the measured levels of biomarkers in a panel, as described herein, and outputting a score. In some embodiments, the measured biomarker levels are test results, which serve as inputs to a computer that is programmed to apply the formula. The system may comprise other inputs in addition to or in combination with biomarker results in order to derive an output score; e.g., one or more clinical parameters such as therapeutic regimen, TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, height, weight, body-mass index, family history, CCP status, RF status, ESR, smoker/non-smoker, etc. In some embodiments the system can apply a formula to biomarker level inputs, and then output a disease activity score that can then be analyzed in conjunction with other inputs such as other clinical parameters. In other embodiments, the system is designed to apply a formula to the biomarker and non-biomarker inputs (such as clinical parameters) together, and then report a composite output disease activity index.

A number of testing systems are presently available that could be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, H J Kisner, "Product development: the making of the Abbott ARCHITECT," Clin. Lab. Manage. Rev. 1997 November-December, 11(6):419-21; A. Ognibene et al., "A new modular chemiluminescence immunoassay analyzer evaluated," Clin. Chem. Lab. Med. 2000 March, 38(3):251-60; J W Park et al., "Three-year experience in using total laboratory automation system," Southeast Asian J. Trop. Med. Public Health 2002, 33 Suppl 2:68-73; D. Pauli et al., "The Abbott Architect c8000: analytical performance and productivity characteristics of a new analyzer applied to general chemistry testing," Clin. Lab. 2005, 51(1-2):31-41.

Another testing system useful for embodiments of the present teachings is the VITROS system (VITROS is a registered trademark of Johnson & Johnson Corp., New Brunswick, N.J.)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes. Such laboratories include, for example, Laboratory Corporation of America, 358 South Main Street, Burlington, N.C. 27215 (corporate headquarters); Quest Diagnostics, 3 Giralda Farms, Madison, N.J. 07940 (corporate headquarters); and other reference and clinical chemistry laboratories.

Kits

Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a MBDA score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the MBDA markers. In various embodiments, the expression of one or more of the sequences represented by the MBDA markers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the inflammatory disease activity of a subject or population over time, or disease activity in response to inflammatory disease treatment, or for drug discovery for inflammatory disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 3. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to monitor the progression or rate of progression of inflammatory disease, or to monitor the effectiveness of treatment for inflammatory disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties,* 1993, W. Freeman and Co.; A. Lehninger, *Biochemistry,* Worth Publishers, Inc. (current addition); J. Sambrook et al., *Molecular Cloning: A Laboratory Manual,* 2nd Edition, 1989; Methods In Enzymology, S. Colowick and N. Kaplan, eds., Academic Press, Inc.; *Remington's Pharmaceutical Sciences,* 18th Edition, 1990, Mack Publishing Company, Easton, Pa.; Carey and Sundberg, *Advanced Organic Chemistry*, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data,* 2nd Edition 2002, John Wiley and Sons, Inc., NJ; M. Pepe, *The Statistical Evaluation of Medical Tests for Classification and Prediction (Oxford Statistical Science Series)* 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction,* Second Edition 2009, Springer, N.Y.; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1: Deriving an MBDA Score

This example demonstrates a method of deriving a Multi-Biomarker Disease Activity (MBDA) score, based on a dataset of quantitative data for biomarkers. In this example, a MBDA score is determined from the biomarker data using an interpretation function that is based on a set of predictive models, where each predictive model is predictive of a component of the DAS28-CRP, in this example TJC, SJC and patient global health assessment (GHA). Deriving an MBDA score as described in this example is described in detail in U.S. Ser. No. 12/905,984, herein incorporated by reference in its entirety.
MBDA Algorithm Development and Evaluation
Training Data A MBDA algorithm was trained using clinical and biomarker data for patients in the InFoRM and BRASS studies. The InFoRM study (Index For Rheumatoid Arthritis Measurement) is a multi-center observational study of the North American RA population. The patients used in algorithm training were recruited between April and September 2009 from 25 sites in the U.S. and Canada. Inclusion criteria were: age >18 years with a diagnosis of RA made by a board-certified rheumatologist. Patients concurrently enrolled in therapeutic drug trials involving a biologic agent and a placebo arm were excluded. The study includes three visits for each patient, each with clinical data and biological sample collection, at approximately three-month intervals.

BRASS is an observational study of approximately 1,000 RA patients receiving care at the RB Brigham Arthritis and Musculoskeletal Diseases Clinical Research Center, at the Brigham and Women's Hospital, Boston, Mass. Inclusion criteria were: age >18 years with a diagnosis of RA made by a board-certified rheumatologist. The study includes annual visits with clinical data and biological sample collection, and patient questionnaires between visits.

The first data set used in training consisted of visit 1 data for 512 InFoRM patients. The 512 patient visits were chosen to have clinical characteristics representative of the entire study population at the time of selection, and also to have been evaluated by a limited number of joint assessors. The number of joint assessors was limited to 12 so that assessor-specific biases could be evaluated and taken into account in algorithm development. The average age of these patients was 58.9 years (range 20-91), and 76% were female. The mean SJC and TJC were 4.28 and 5.49, respectively.

Assays for 25 candidate biomarkers were run on serum from the 512 InFoRM visits. Those biomarkers were SAA1, IL6, TNFRSF1A, VEGFA, PYD, MMP1, ICAM1, calprotectin, CHI3L1 (YKL40), MMP3, EGF, IL1RA, VCAM1, LEP, RETN, CRP, IL8, APOA1, APOC3, CCL22, IL1B, IL6R, IL18, keratan sulfate and ICTP. All the biomarker assays were run on the Meso Scale Discovery (MSD®) platform. See Example 1 of US 2011/0137851 for specifics of biomarker assay development and evaluation.

The biomarkers were prioritized based on (1) univariate association with disease activity, (2) contribution to multivariate models for disease activity, and (3) assay performance.

The assays for 20 candidate biomarkers were run in a second set of patient samples, comprising 167 samples from BRASS and 29 from InFoRM. These 20 candidate biomarkers were SAA1, IL6, TNFRSF1A, VEGFA, PYD, MMP1, ICAM1, calprotectin, YKL40, MMP3, EGF, IL1RA, VCAM1, leptin, resistin, CRP, IL8, CCL22, IL1B and IL6R. The samples were selected to enrich the overall training data for extremes of disease activity, while also having good representation of patients with moderate disease activity. Enriching for extreme phenotypes can result in improved algorithm training, as long as the resulting training population still fully represents the types of patients on which the algorithm will used in independent validation and intended use populations. The 167 BRASS samples were intended to represent similar numbers of patients with low, moderate and high disease activity. The 29 InFoRM samples were selected to represent patients with high disease activity, since low and moderate activity patients were already well represented by the first 512 training samples.
Data Analysis Prior to statistical analyses, all assay data were reviewed for pass/fail criteria on parameters including inter-assay CV, intra-assay CV, percent of samples within the measureable range of the calibration curve, and four serum process controls within the range of the calibration curve. The biomarker values that were not in the measureable range of the calibration curves were marked as missing data, and imputed with the lowest/highest detected value across all the samples within a given biomarker assay during the data export process. If the intra-assay CV of the biomarker concentration, computed from two replicates, was greater than 30%, it was also considered missing and excluded from univariate analyses. For multivariate analysis, individual biomarkers were excluded entirely if more than 20% of their data values were missing, and other missing data were imputed by the KNN algorithm (with k=5 nearest neighbors). In the data used for algorithm training, no biomarkers were excluded from multivariate analysis because they all had less than 20% missing values. Concentration values were transformed as x0.1 prior to further analysis in order to make the distribution of values for each biomarker more normal. This transformation has a similar effect to log transformation but avoids the generation of negative values. The transformed, imputed biomarker dataset is denoted as X_(n×m), where X is the protein data from n markers and m samples.

In univariate analysis, the Pearson correlations between the levels of each biomarker and disease activity measures including DAS28-CRP4, DAS28-ESR4, SJC, TJC, GHA, SDAI and CDAI were calculated.

In multivariate analysis, statistical models were developed by five different regression methods. In the first regression method (1), forward stepwise ordinary least square regression, the equation $Y=X\beta+\varepsilon$ applies, where Y is the column vector with observed values, $\beta$ is the vector of coefficients, and $\varepsilon$ is the residuals. The forward selection begins with no variables in the model. Then, given a collection of predictors X, the one having the largest absolute correlation with the response Y is selected and a simple linear regression of Y on X1 is performed. The residual vector is now orthogonal to X1, and is taken to be the new response variable. The other predictors are then projected orthogonally to X1 and the forward selection process is repeated.

In the second method (2), Lasso is used to prioritize biomarkers (based on $R^2$ values) and to obtain a Lasso model. The "lasso" in this model minimizes the residual sum of squares, subject to the sum of the absolute value of the coefficients being less than a constant. This method produces interpretable models and exhibits the stability of ridge regression. See R. Tibshirani, *J. Royal Stat. Soc. B* 1996, 58(1):267-288.

In the third method (3), the Elastic Net, mixtures of Lasso and ridge penalties are applied. It encourages a grouping effect, where strongly correlated predictors segregate together, either tending to be in or out of the model together. See T. Zou, *J. Royal Stat. Soc. B* 2005, 67(2):301-320. For each of the above three methods, the marker selected at each step is recorded.

The fourth method (4) is Multivariate Response with Curds and Whey (CW) using ordinary least squares (OLS). See L. Breiman and J H Friedman, *J. Royal. Stat. Soc. B* 1997, 59(1):3-54. This method takes advantage of the correlations between the response variables (e.g., components of DAS) to improve predictive accuracy, compared with the usual procedure of performing an individual regression of each response variable on the common set of predictor variables X. In CW, $Y=XB*S$, where $Y=(y_{kj})$ with k for the $k^{th}$ patient and j for $j^{th}$ response (j=1 for TJC, j=2 for SJC, etc.), B is obtained using OLS, and S is the shrinkage matrix computed from the canonical co-ordinate system. Hence, this approach will yield sub-models corresponding to each component of DAS.

The fifth method (5) is Curds and Whey and Lasso in combination (CW-Lasso). Instead of using OLS to obtain B as in CW, Lasso was used, and the parameters were adjusted accordingly for the Lasso approach.

The performance of the five regression methods was compared in 70/30 cross validation (repeatedly training in a randomly selected 70% of the data and testing in the remaining 30%). The number of markers in each regression model chosen by using nested 10-fold cross-validation once the number of markers was selected for a given analysis method the best-fitting model of that size was used to represent the method. In the CW approaches (methods 4 and 5), nested 10 fold cross validation was used for each sub-model corresponding to each component of DAS. The models developed using the CW-Lasso method performed best overall. The following sections consist of results mainly using CW-Lasso approach.

The 20 candidate biomarkers examined in all training samples were prioritized according to a number of criteria, including: strength of association with disease activity and contribution to multivariate models; consistency of correlation with disease activity across feasibility and training data sets; CRP was excluded from any sub-models for TJC, SJC, and PGA both because it is included in the DAS28-CRP4 and because it did not increase sub-model prediction accuracy in independent test samples (CRP is used, however, in the final MBDA score calculation as part of the MBDA formula); robust assay performance (IL1B was excluded from final modeling because its concentrations too frequently fall below the limits of detection of immunoassays); known drug effects (IL6R was excluded from final modeling because it is known to be strongly affected by tocilizumab, independently of the effects of the drug on disease activity); and, stability (IL8 was excluded from final modeling because its measurable levels are known to rise dramatically when serum samples are not kept cold). These criteria led to 15 candidate biomarkers being considered for inclusion in the final algorithm. See Table 1.

TABLE 1

| Biomarker | Functional Category |
|---|---|
| calprotectin | cytokines and receptors |
| CHI3L1 | skeletal |
| EGF | growth factors |
| ICAM1 | adhesion molecules |
| IL1RA | cytokines and receptors |
| IL6 | cytokines and receptors |
| LEP | hormones |
| MMP1 | matrix metalloproteinases |
| MMP3 | matrix metalloproteinases |
| PYD | skeletal |
| RETN | hormones |
| SAA1 | acute phase response |
| TNFRSF1A | cytokines and receptors |
| VCAM1 | adhesion molecules |
| VEGFA | growth factors |

Training the Algorithm

While all data was used in prioritizing biomarkers, a subset was used for training the final algorithm. This subset was selected to have a broad range of disease activity levels, so that patients at all levels of disease activity were well represented. A comparison was made of the performance of models trained using: only BRASS samples (167 total); BRASS samples plus InFoRM samples (167+~100) selected to have a uniform disease activity distribution; or, BRASS samples plus InFoRM samples (167+~100) with a disease activity distribution like that of the BRASS samples.

The model performance was evaluated in an independent set of BRASS and InFoRM samples (70 total) set aside for this purpose. The DAS28-CRP distribution of this independent test set was similar to that of past studies (approximately normal). As shown below, correlation (r) to the DAS28-CRP and area under the ROC curve (AUROC) for predicting high and low DAS using median cut off were higher when training used BRASS samples plus "BRASS-like" InFoRM samples, although the differences were not statistically significant. The following Table 2 uses the Lasso regression method.

TABLE 2

| Training Set | r | AUROC |
|---|---|---|
| BRASS only | 0.53 | 0.68 |
| BRASS + Uniform InFoRM | 0.54 | 0.69 |
| BRASS + BRASS-like InFoRM | 0.55 | 0.71 |

For final training, the combination of BRASS plus "BRASS-like" InFoRM samples was selected. The CW-Lasso regression method was chosen for development of the final algorithm because of its superior performance in cross validation within the training set and in testing using InFoRM 512 patients and CAMERA patients (see below, MBDA algorithm performance, for a description of algorithm testing in another cohort of samples). In the application of this method, the shrinkage matrix was applied to the predictions of TJC and SJC. Ten-fold cross-validation indicated that the following 13 markers were optimal for performance. See Table 3.

TABLE 3

| Marker | TJC | SJC | PGA |
|---|---|---|---|
| calprotectin | X | | |
| CHI3L1 | X | X | |
| EGF | X | X | X |
| IL6 | X | X | X |
| LEP | X | | X |
| MMP1 | | | X |
| MMP3 | | | X |
| PYD | X | X | |
| RETN | | | X |
| SAA1 | X | X | X |
| TNFRSF1A | X | | X |
| VCAM1 | X | | X |
| VEGF1 | X | | X |

From this set, PYD and calprotectin were excluded due to elevated assay failure rates. The remaining 11 biomarkers gave very similar algorithm performance to the full set of 13. An algorithm was chosen for validation that was developed by CW-Lasso regression using this 11-marker to estimate the DAS28-CRP in data from the BRASS+BRASS-like InFoRM samples. The estimates of TJC, SJC and PGHA were combined with a CRP test result in a formula similar to that used to calculate the DAS28-CRP.

$$DAS28CRP = 0.56\sqrt{TJC} + 0.28\sqrt{SJC} + 0.14PGHA + 0.36\log\left(\frac{CRP}{10^6} + 1\right) + 0.96$$

$$PDAS = 0.56\sqrt{IPTJC} + 0.28\sqrt{IPSJC} + 0.14PPGHA + 0.36\log\left(\frac{CRP}{10^6} + 1\right) + 0.96$$

Here IPTJC=Improved Prediction of TJC, IPSJC=Improved Prediction of SJC, PPGHA=Predicted PGHA, and PDAS is Predicted DAS28-CRP. (Details are defined below; see Selected algorithm). The MBDA score is the result from this formula.

Table 4 demonstrates the correlation of the values predicted by the PDAS algorithm with actual values for TJC, SJC, PGHA and DAS28-CRP, in the two cohorts studied, CAMERA and InFoRM.

TABLE 4

| Study | TJC | SJC | PGHA | DAS28-CRP |
|---|---|---|---|---|
| CAMERA | 0.445 | 0.536 | 0.427 | 0.726 |
| InFoRM (512 subjects) | 0.223 | 0.328 | 0.388 | 0.53 |

Selected Algorithm

The 11-marker+CRP Lasso model selected from the training process is as follows:

PTJC=−38.564+3.997*(SAA1)$^{1/10}$+17.331*(IL6)$^{1/10}$+ 4.665*(CHI3L1)$^{1/10}$−15.236*(EGF)$^{1/10}$+2.651* (TNFRSF1A)$^{1/10}$+2.641*(LEP)$^{1/10}$+4.026* (VEGFA)$^{1/10}$−1.47*(VCAM1)$^{1/10}$;

PSJC=−25.444+4.051*(SAA1)$^{1/10}$+16.154*(IL6)$^{1/10}$− 11.847*(EGF)$^{1/10}$+3.091*(CHI3L1)$^{1/10}$+0.353* (TNFRSF1A)$^{1/10}$;

PPGHA=−13.489+5.474*(IL6)$^{1/10}$+0.486* (SAA1)$^{1/10}$+2.246*(MMP1)$^{1/10}$+1.684* (leptin)$^{1/10}$+4.14*(TNFRSF1A)$^{1/10}$+2.292* (VEGFA)$^{1/10}$−1.898*(EGF)$^{1/10}$+0.028* (MMP3)$^{1/10}$−2.892*(VCAM1)$^{1/10}$−0.506* (RETN)$^{1/10}$;

IPTJC=max(0.1739*PTJC+0.7865*PSJC,0);

IPSJC=max(0.1734*PTJC+0.7839*PSJC,0);

*MBDA* score=round(max(min((0.56*sqrt(IPTJC)+ 0.28*sqrt(IPSJC)+0.14*PPGA+0.36*ln(CRP/ 10$^6$+1))*10.53+1,100),1)).

For the final DA algorithm, the results from the 11-marker+CRP CW-Lasso model were scaled and rounded to be integers on a scale of 1-100 such that a MBDA score of 1 would be equivalent to a DAS28-CRP value of 0, and a MBDA score of 100 would be equivalent to a DAS28-CRP value of 9.4.

Gene names in the above formulas correspond to serum protein concentrations, as obtained by the MSD® platform. Biomarker concentrations were obtained in the ranges shown in Table 5 (95% interval).

TABLE 5

| | pg/ml | |
|---|---|---|
| Biomarker | Lower Limit | Upper Limit |
| IL6 | 2.2 | 104 |
| EGF | 20 | 383 |
| VEGFA | 83 | 776 |
| LEP | 2,226 | 139,885 |
| SAA1 | 636,889 | 99,758,140 |
| VCAM1 | 354,026 | 1,054,681 |
| CRP | 245,332 | 76,399,801 |
| MMP1 | 3,047 | 39,373 |
| MMP3 | 9,203 | 134,262 |
| TNFRSF1A | 1,139 | 4,532 |
| RETN | 3,635 | 19,308 |
| CHI3L1 | 25,874 | 442,177 |

MBDA Algorithm Performance

In order to independently test the performance of the algorithm developed above in this Example, a total of 120 serum samples were analyzed, obtained from the CAMERA study. Samples were obtained from the Computer Assisted Management in Early Rheumatoid Arthritis Study (CAMERA). From 1999-2003, all early rheumatoid arthritis patients (i.e., disease duration of one year or less) who fulfilled the 1987 revised American College of Rheumatology (ACR) criteria for rheumatoid arthritis were asked to participate in this two-year randomized, open-label prospective multicentre strategy trial. As a result, 299 patients were studied. Patients visited the outpatient clinic of one of the six rheumatology departments in the region of Utrecht, the Netherlands, collaborating in the Utrecht Rheumatoid Arthritis Cohort study group. Inclusion criteria were that patients must have exhibited symptoms for less than one year, with age greater than 16 years. Exclusion criteria were the previous use of glucocorticoids or any DMARD, use of cytotoxic or immunosuppressive drugs within a period of three months before inclusion, alcohol abuse, defined as more than two units per day, and psychological problems, which would make adherence to the study protocol impossible. At baseline all patients were monitored for medical conditions that would interfere with MTX usage. This screening included a chest X-ray, liver enzymes, albumin, hepatitis serology, serum creatinine and complete blood count. An independent person performed randomization in blocks of nine per hospital. The medical ethics committees of all participating hospitals approved this study, and all patients gave written informed consent before entering the study.

The cohort for this study had the following characteristics: 69% female, 68% CCP positive, 74% RF positive, 100% on MTX, 100% on non-biologic DMARDs, and 0% on biologic DMARDs. Additionally, the mean age of the cohort was 52 years (standard deviation (SD)+/−14.7), with a minimum age of 17 and a maximum age of 78. The mean DAS28-CRP for this cohort was 5.0 (SD+/−1.9), with a minimum of 0.9 and a maximum of 8.4.

A subpopulation of 72 subjects was selected from the CAMERA cohort for this Example. All 72 patients were represented by baseline (time 0) visits and samples, and 48 were also represented by six-month visits and samples. Within the visits selected, a wide distribution of DAS28-CRP scores were represented, ranging from a minimum of 0.96 to a maximum of 8.4.

Of these, 72 samples were taken from subject baseline visits, and 48 were from visits six months subsequent to baseline. The concentrations of 23 serum protein biomarkers were measured in each sample: APOA1, APOC3, calprotectin, CCL22, CHI3L1 (YKL40), CRP, EGF, ICAM1, IL18, IL1B, IL1RA, IL6, IL6R, IL8, LEP, MMP1, MMP3, PYD, REIN, SAA1, TNFRSF1A, VCAM1, and VEGFA. The concentrations of the markers were determined by customized immunoassays using either the Meso Scale Discovery SECTOR® Imager 6000 or individual ELISAs.

The associations between individual biomarkers and the clinical assessment measurements of DAS28-CRP, SJC28 and TJC28 were assessed by Pearson correlation (r) for log-transformed concentrations. The correlation p-values were adjusted for multiple hypothesis testing by estimating false discovery rates (FDR) using the method of Benjamin and Hochberg. See *J. Royal Stat. Soc. B* 1995 57(1):289-300.

Of the 23 proteins examined, fourteen were statistically significantly correlated with DAS28-CRP, eleven with SJC28 and nine with TJC28 (FDR<0.05). See Table 6, which shows the Pearson correlations (r) between individual biomarkers and each clinical disease activity measure. The q-values reflect the FDRs, and were calculated by adjusting the p-values for multiple hypothesis testing. Statistically significant associations (q<0.05) are in bold. As Table 6 shows, the individual biomarkers associated with disease activity represented a range of pathways associated with RA disease pathophysiology (Functional Category).

TABLE 6

| Biomarker | Functional Category | DAS28-CRP r | DAS28-CRP q-val | SJC28 r | SJC28 q-val | TJC28 r | TJC28 q-val |
|---|---|---|---|---|---|---|---|
| calprotectin | cytokines and receptors | 0.56 | <0.01 | 0.38 | <0.01 | 0.33 | <0.01 |
| CHI3L1 | Skeletal | 0.42 | <0.01 | 0.35 | <0.01 | 0.30 | <0.01 |
| CCL22 | cytokines and receptors | −0.04 | 0.75 | −0.13 | 0.19 | −0.03 | 0.73 |
| CRP | acute phase response | 0.69 | <0.01 | 0.41 | <0.01 | 0.36 | <0.01 |
| EGF | growth factors | −0.07 | 0.46 | −0.08 | 0.42 | −0.12 | 0.28 |
| ICAM1 | adhesion molecules | 0.23 | 0.02 | 0.13 | 0.20 | 0.08 | 0.44 |
| IL1B | cytokines and receptors | 0.45 | <0.01 | 0.34 | <0.01 | 0.31 | <0.01 |
| IL6 | cytokines and receptors | 0.69 | <0.01 | 0.50 | <0.01 | 0.41 | <0.01 |
| IL6R | cytokines and receptors | 0.01 | 0.97 | 0.03 | 0.71 | 0.02 | 0.89 |
| IL8 | cytokines and receptors | 0.47 | <0.01 | 0.46 | <0.01 | 0.30 | <0.01 |
| IL1RA | cytokines and receptors | 0.01 | 0.97 | 0.05 | 0.58 | −0.09 | 0.44 |
| LEP | hormones | 0.00 | 0.97 | −0.07 | 0.53 | −0.06 | 0.56 |
| MMP1 | MMPs | 0.36 | <0.01 | 0.29 | <0.01 | 0.19 | 0.06 |
| MMP3 | MMPs | 0.51 | <0.01 | 0.40 | <0.01 | 0.26 | <0.01 |
| PYD | skeletal | 0.23 | 0.04 | 0.29 | <0.01 | 0.21 | 0.09 |
| RETN | hormones | 0.22 | 0.03 | 0.13 | 0.20 | 0.13 | 0.28 |
| SAA1 | acute phase response | 0.66 | <0.01 | 0.43 | <0.01 | 0.37 | <0.01 |
| TNFRSF1A | cytokines and receptors | 0.36 | <0.01 | 0.30 | <0.01 | 0.24 | 0.02 |
| VCAM1 | adhesion molecules | 0.13 | 0.24 | 0.14 | 0.20 | 0.08 | 0.56 |
| VEGFA | growth factors | 0.29 | <0.01 | 0.18 | 0.12 | 0.07 | 0.56 |

Two pre-specified algorithms, a prototype and a final algorithm, using subsets of these 23 biomarkers were applied to calculate a total MBDA score for each subject at each visit (baseline and six-month). These algorithms were trained in prior studies using independent samples from other clinical cohorts. Algorithm performance was evaluated by Pearson correlation (r) and area under the ROC curve (AUROC) for identifying high and low disease activity at the baseline and six-month visits. The reference classification for ROC analysis was based on a DAS28-CRP of 2.67, the threshold separating remission/low disease activity from moderate and high disease activity.

Prototype Algorithm for Multivariate Model

The first algorithm, or "prototype algorithm," using a linear combination of protein biomarkers, was trained on subject samples to estimate the DAS28 directly and was provided by the formula described elsewhere herein according to:

$$MBDA = b_0 + b_1 * DAIMRK_1^x - b_2 * DAIMRK_2^x - b_3 * DAIMRK_3^x \ldots - b_n * DAIMRK_n^x;$$

where MBDA is the MBDA score, $b_{0-n}$ are constants, and $DAIMRK_{1-n}^x$ are the serum concentrations, transformed to the $x^{th}$ power, of n different biomarkers selected from the panel of biomarkers.

The prototype algorithm used in this Example was:

$$MBDA = (-16.1564) - (0.0606 * Calprotectin^{1/10}) + (0.2194 * CHI3L1^{1/10}) + (1.1886 * ICAM1^{1/10}) + (2.7738 * IL6^{1/10}) + (0.7254 * MMP1^{1/10}) - (0.8348 * MMP3^{1/10}) + (1.0296 * PYD^{1/10}) + (1.1792 * SAA1^{1/10}) + (2.4422 * TNFRSF1A^{1/10}) + (0.3272 * VEGFA^{1/10}).$$

The prototype algorithm achieved a Pearson correlation (r) of 0.65 and an AUROC of 0.84 relative to the DAS28-CRP.

Biomarker Selection for Final Algorithm

The second algorithm was derived using serum biomarker concentrations to separately estimate the three clinical assessments of TJC28, SJC28 and PGHA. Note that all of these are components of the formula used in calculating DAS28-CRP:

$$DAS28\text{-}CRP=0.56*sqrt(TJC28)+0.28*sqrt(SJC28)+0.36*\ln(CRP+1)+(0.014*PGHA)+0.96.$$

Figure 2:
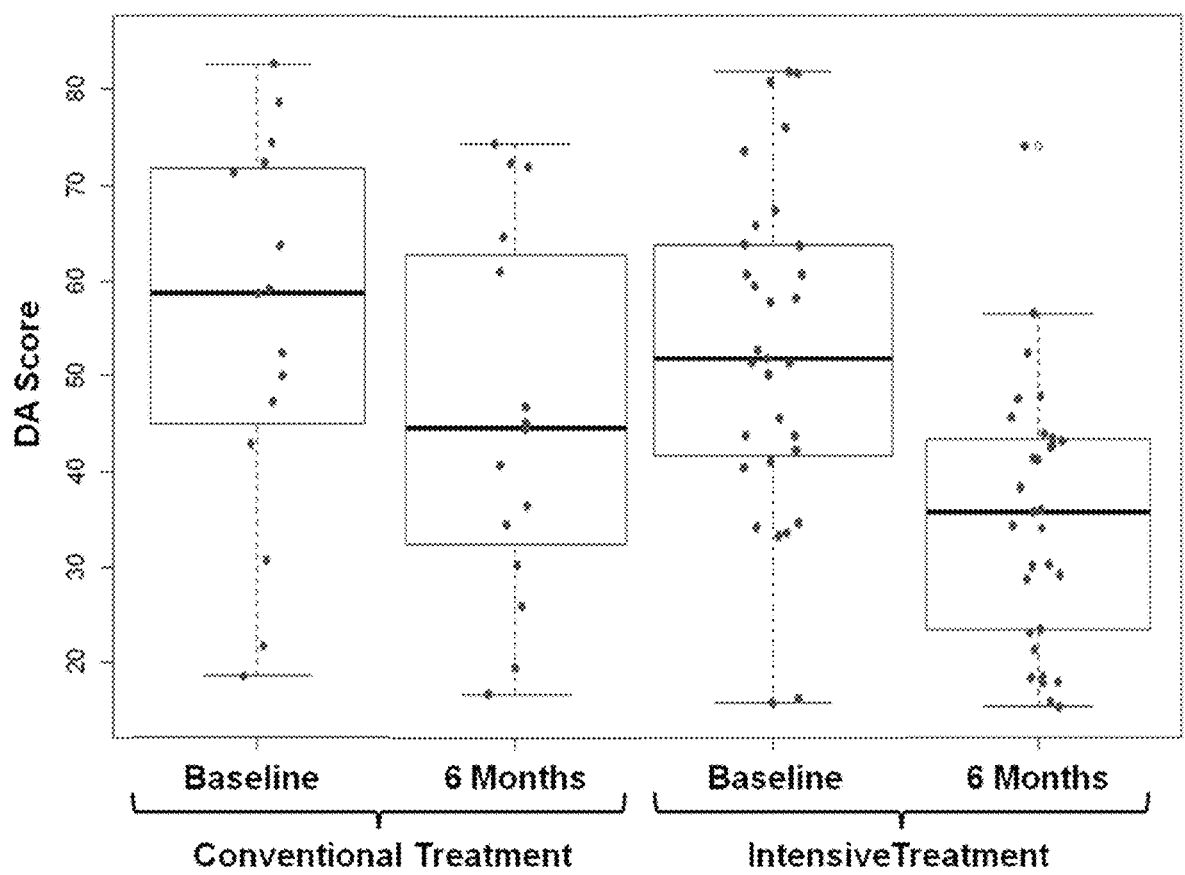
FIG. 2 depicts the MBDA scores for subjects at baseline and six-month visits, according to the description in Example 1. MBDA scores are shown by treatment arm and time point. Only subjects with MBDA scores available at both baseline and six months are shown.

Biomarkers were then selected to predict and estimate clinical assessments of disease activity, specifically PGHA, TJC28 and SJC28. The resulting estimates were combined with a serum CRP concentration measurement to calculate an overall MBDA score. See FIG. 2, which indicates the three panels of biomarkers predictive of clinical disease activity measurements, the union thereof, and CRP. The CW-Lasso method was used to predict the individual components of the DAS28; i.e., TJC28, SJC28 and PGHA. Note that biomarker terms are included in the CW-Lasso if they help to improve cross-validated model performance, and this criterion does not imply that each term is statistically significant by univariate analysis. A biomarker could make a significant contribution to a multivariate model even if it does not have a significant univariate correlation, and could not make a significant contribution to a multivariate model even though it has a significant univariate correlation. Indeed, a comparison of each algorithm predictive for a clinical assessment, (a)-(c) above, with the biomarkers of Table 3 shows that not all biomarkers in each algorithm were individually statistically correlated with that clinical assessment. For example, values for serum concentrations of EGF, LEP, VEGFA and VCAM1 are all included in the algorithm for predicting TJC28, yet each of these markers individually demonstrated a q-value for correlation with TJC of ≥0.28. Including these markers, however, improves multivariate model performance in independent cross-validation test sets.

The overall MBDA score derived according to the methods of the present Example was given as a whole number between 1 and 100. The formula used to derive this score was provided by:

$$MBDA\ Score=((0.56*sqrt(PTJC)+0.28*sqrt(PSJC)+0.36*\log(CRP/10^6+1)+(0.14*PPGHA)+0.96)*10.53)+1,$$

where PTJC=predicted TJC28, PSJC=predicted SJC28, and PPGHA=predicted PGA. This examples includes data from the following set of biomarkers: SAA1, IL6, CHI3L1, EGF, TNFRSF1A, LEP, VEGFA and VCAM1 for PTJC; SAA1, IL6, EGF, CHI3L1 and TNFRSF1A for PSJC; SAA1, MMP1, LEP, TNFRSF1A, VEGFA, EGF, MMP3, VCAM1 and RETN for PPGHA; plus CRP. In total, therefore, data from the following set of 12 markers was used to derive a MBDA score: CHI3L1, CRP, EGF, IL6, LEP, MMP1, MMP3, RETN, SAA1, TNFRSF1A, VCAM1 and VEGFA. The predicted clinical assessments of disease activity were developed according to the following formulas:

$$PTJC=-38.564+(3.997*SAA1^{1/10})+(17.331*IL6^{1/10}+(4.665*CHI3L1^{1/10})-(15.236*EGF^{1/10})+(2.651*TNFRSF1A^{1/10})+(2.641*LEP^{1/10})+(4.026*VEGFA^{1/10})-(1.47*VCAM1^{1/10});\quad(a)$$

$$PSJC=-25.444+(4.051*SAA1^{1/10})+(16.154*IL6^{1/10}-(11.847*EGF^{1/10})+(3.091*CHI3L1^{1/10})+(0.353*TNFRSF1A^{1/10};\ and,\quad(b)$$

$$PPGHA=-13.489+(5.474*IL6^{1/10}+(0.486*SAA1^{1/10})+(2.246*MMP1^{1/10})+(1.684*LEP^{1/10}+(4.14*TNFRSF1A^{1/10})+(2.292*VEGFA^{1/10})-(1.898*EGF^{1/10})+(0.028*MMP3^{1/10})-(2.892*VCAM1^{1/10})-(0.506*RETN^{1/10}).\quad(c)$$

The performance of the above algorithm in deriving a MBDA score was evaluated by Pearson correlation (r) and area under the ROC curve (AUROC) for identifying high and low disease activity at the baseline and six-month visits. The Pearson correlation was 0.73, and the AUROC was 0.87, with the reference classification for ROC analysis based on a threshold DAS28-CRP of 2.67, the threshold separating remission/low disease activity from moderate and high disease activity. The changes in biomarker-based MBDA scores between the baseline and six-month visits were assessed by the paired Wilcoxon rank sum test.

To ensure that performance of the second algorithm was not overestimated due to the inclusion of two samples for some patients, subsets of samples were also analyzed that included only one randomly selected visit for each subject. The algorithm performed equally well in these subsets. Possible bias in the AUROC due to an imbalance in numbers between low and high disease activity groups was also analyzed using a DAS28-CRP cutoff of 2.67. When the cutoff was set at the median DAS28-CRP of 4.6, the AUROC was 0.83.

When the predictions of the individual components of the DAS28 generated by the MBDA algorithm were correlated to the actual TJC28, SJC28 and PGHA, the correlation coefficients were seen to trend higher (and thus provide better correlation with clinical disease activity measurements) than the coefficients for CRP, a marker commonly used alone as an indicator of RA disease activity. See FIG. 1.

An analysis was then done to determine whether the MBDA score changed in response to the treatment protocols used in the CAMERA study. For all subjects for whom MBDA Scores were available for both visits (baseline and six-month), the median score dropped from 52 to 37 (p=2.2E-6; n=46). See FIG. 2. The intensive and conventional treatment arms were considered separately. There was also a significant decrease in median MBDA Score in the intensive treatment arm, from 52 to 36 (p=2.5E-5; n=31). In the conventional treatment arm, the median MBDA Score decreased from 59 to 45 (p=0.06; n=15).

In conclusion, this Example demonstrates that serum protein biomarkers representing a variety of biological pathways were consistently associated with RA disease activity. A pre-specified MBDA algorithm combining information from several of these biomarkers performed well in predicting RA disease activity when evaluated in an independent test set. The algorithm's estimates of TJC, SJC and PGHA correlated to actual clinical measures of disease activity. Furthermore, subsequent MBDA scores of the subjects analyzed decreased compared to initial MBDA scores following and in response to treatment.

Example 2: Use of MBDA Score to Assess Psoriatic Arthritis Disease Activity

This example demonstrates that the MBDA score described in Example 1 can be used to assess disease activity in Psoriatic Arthritis (PsA) patients.

The considerable heterogeneity in clinical domains of involvement of PSA can make assessment of disease activity challenging. As a result, there has been interest in developing biomarkers to assess disease activity. The MBDA assay described in Example 1, which is a weighted composite of 12 serum protein biomarkers, has been shown to correlate with disease activity in rheumatoid arthritis (Curtis J R, et al. *Arthritis Care Res* 64: 1794-1803 (2012)). The objective of this example was to investigate if the biomarker panel of the MBDA test correlated with disease activity across different domains of PsA.

Methods

A cross-sectional sample of 30 adult patients with PsA fulfilling CASPAR criteria was recruited from UCSD Arthritis Clinics (Taylor W, et al. *Arthritis Rheum* 54:2665-73 (2006)). Clinical data and serum samples were collected and serum was analyzed for MBDA score and its individual biomarkers (Hambardzumyan K, et al. *Ann Rheum Dis.* 74:1102-9 (2015)) and ICAM-1, IL-6R, and MDC.

Table 7 describes the characteristics of the 30 patients of this Example.

TABLE 7

| | |
|---|---|
| Gender (male), N(%) | 15 (50.0) |
| Age (years), mean ± SE | 49.5 ± 11.2 |
| Psoriatic arthritis duration (years), mean ± SE | 7.9 ± 8.9 |
| Psoriasis duration (years), mean ± SE | 14.7 ± 13.6 |
| Skin psoriasis (PASI), N (%) | 23 (76.7) |
| Skin BSA (%), mean ± SE | 9.0 ± 23.0 |
| Enthesitis, N (%) | 8 (26.7) |
| Dactylitis, N (%) | 2 (6.7) |
| Nail psoriasis, N (%) | 15 (50.0) |
| Tender joint count 28 joints, mean ± SE | 2.9 ± 4.4 |
| Swollen joint count 28 joints, mean ± SE | 2.7 ± 3.4 |
| Physician global (VAS 0-10 cm), mean ± SE | 4.4 ± 3.3 |
| HAQ score, mean | 0.7 ± 0.7 |
| CDAI, mean | 13.2 ± 11.5 |
| DAS28, mean | 2.68 ± 1.75 |
| DAS28-CRP, mean | 2.61 ± 1.25 |
| Current biologics, N (%) | 15 (50.0) |
| Current DMARDs, N (%) | 14 (46.7) |
| Current NSAIDs, N (%) | 12 (40.0) |
| Current topical therapy, N (%) | 10 (33.3) |

Results

The average MBDA score was 39.6, which would be consistent with a moderate disease activity score in RA (Curtis et al., (2012). In the PsA cohort, the MBDA score was most strongly correlated with physician global assessment (Pearson correlation coefficient, r=0.57), DAS28 (r=0.53), and skin BSA (r=0.50). Correlations were poorer with CDAI (r=0.35), SJC28 (R=0.35), patient global assessment (r=−0.08), HAQ score (r=0.15), and pain score (r=0.12). Analysis of individual biomarkers showed strong correlations, in many cases higher than for the composite MBDA score: SAA, INFRI, MDC, and leptin with skin BSA (r=0.85, 0.84, 0.75, and 0.72, respectively); leptin and ICAM-1 with DAS29 score (r=0.62 and 0.52, respectively); and SAA and VCAM-1 with PhGA (r=0.67 and 0.61, respectively). These data suggest the MBDA score derived in Example 1 can correlate with disease activity in PsA.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A method for treating a subject having psoriatic arthritis (PsA), the method comprising:
    performing at least one immunoassay on a blood sample from the subject to generate a dataset comprising protein level data for protein markers from a set comprising chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and vascular endothelial growth factor A (VEGFA);
    calculating, using the protein level data, a PsA disease activity, wherein the PsA disease activity is significantly greater than found for a combination of control biomarkers that are indicative of PsA; and
    administering a PsA therapeutic regimen to the subject in need thereof, wherein the therapeutic regimen comprises one or more of:
        administering a therapeutic compound selected from disease-modifying antirheumatic drugs (DMARDs), biologic DMARDs, non-steroidal anti-inflammatory drugs (NSAIDs), and corticosteroids;
        administering physical therapy, dietary modification and/or supplementation; and
        administering bariatric surgical intervention.

2. The method of claim 1, wherein performance of the at least one immunoassay comprises:
    obtaining a blood sample from the subject, wherein the blood sample comprises the protein markers;
    contacting the blood sample with a plurality of distinct reagents;
    generating a plurality of distinct complexes between the reagents and the protein markers; and
    detecting the complexes to generate the protein level data.

3. The method of claim 1, wherein the at least one immunoassay comprises a multiplex assay.

4. The method of claim 1, wherein the protein markers consist of at most 500 protein markers.

5. The method of claim 4, wherein the protein markers consist of at most 250 protein markers.

6. The method of claim 4, wherein the protein markers consist of at most 100 protein markers.

7. The method of claim 4, wherein the protein markers consist of at most 50 protein markers.

8. The method of claim 4, wherein the protein markers consist of at most 25 protein markers.

9. The method of claim 4, wherein the protein markers consist of 12 protein markers.

10. The method of claim 1, wherein the PsA disease activity is calculated using an interpretation function comprising the protein level data and values of one or more clinical assessments of the subject.

11. The method of claim 10, wherein the interpretation function comprises a predicted Tender Joint Count 28 (TJC28) value, a predicted Swollen Joint Count28 (SJC28) value, and a predicted Patient Global Health (PGA) value.

12. The method of claim 11, wherein the predicted values were obtained by Curds and Whey and Lasso (CW-Lasso).

13. The method of claim 11, wherein the interpretation function is given by the formula: score=$((0.56\times(\text{predicted TJC28})^{0.5}+0.28\times(\text{predicted SJC28})^{0.5}+0.36\times\log(\text{CRP}\times 10^{-6}+1)+(0.14\times(\text{predicted PGA}))+0.96)\times 10.53)+1$.

* * * * *